(12) United States Patent
Shinohara et al.

(10) Patent No.: US 9,324,602 B2
(45) Date of Patent: Apr. 26, 2016

(54) SUBSTRATE INVERTING APPARATUS AND SUBSTRATE PROCESSING APPARATUS

(71) Applicant: SCREEN Holdings Co., Ltd., Kyoto (JP)

(72) Inventors: Takashi Shinohara, Kyoto (JP); Jun Shibukawa, Kyoto (JP); Hiroshi Kato, Kyoto (JP)

(73) Assignee: SCREEN Holdings Co., Ltd., Kyoto (JP)

( * ) Notice: Subject to any disclaimer, the term of this patent is extended or adjusted under 35 U.S.C. 154(b) by 0 days.

(21) Appl. No.: 14/403,221

(22) PCT Filed: Feb. 28, 2013

(86) PCT No.: PCT/JP2013/055452
§ 371 (c)(1),
(2) Date: Nov. 24, 2014

(87) PCT Pub. No.: WO2013/187090
PCT Pub. Date: Dec. 19, 2013

(65) Prior Publication Data
US 2015/0131088 A1    May 14, 2015

(30) Foreign Application Priority Data
Jun. 15, 2012  (JP) ................................. 2012-135999

(51) Int. Cl.
*G01N 21/95* (2006.01)
*B25J 11/00* (2006.01)
(Continued)

(52) U.S. Cl.
CPC ....... *H01L 21/68707* (2013.01); *B25J 11/0095* (2013.01); *G01N 21/9501* (2013.01); *H01L 21/67046* (2013.01); *H01L 21/67781* (2013.01); *G01N 2201/06113* (2013.01)

(58) Field of Classification Search
USPC ........ 356/399, 401; 414/403, 416.01, 226.01, 414/222.01, 217; 134/33, 32, 42; 156/64, 156/556, 378
See application file for complete search history.

(56) References Cited

U.S. PATENT DOCUMENTS 5,498,294 A     3/1996   Matsushita et al. ............... 134/6
6,079,073 A *   6/2000   Maekawa ............... B08B 1/007
                                                    15/102

(Continued)

FOREIGN PATENT DOCUMENTS

JP      6-163493        6/1994
JP      H09-232405 A    9/1997

(Continued)

OTHER PUBLICATIONS

Taiwanese Office Action issued on Feb. 13, 2015 in connection with Taiwanese Application No. 102106585 with English and Japanese translation of relevant parts.

(Continued)

*Primary Examiner* — Sang Nguyen
(74) *Attorney, Agent, or Firm* — Ostrolenk Faber LLP

(57) ABSTRACT

Provided is a technique which can properly invert a plurality of substrates at a time. To achieve this object, a substrate inverting apparatus includes: a support mechanism which supports a plurality of substrates in a state where the substrates are stacked vertically in a spaced-apart manner in a horizontal posture; and a clamping and inverting mechanism which clamps the plurality of substrates supported by the support mechanism respectively and inverts the plurality of substrates at a time. In the support mechanism, support members which support the substrate are moved to a standby position from a support position while being moved downward away from the center of the substrate as viewed in the vertical direction. On the other hand, in the clamping and inverting mechanism, clamping members which clamp the substrate are moved to a near position from a remote position by a clamping member drive part and are elastically biased by an elastic member toward side surfaces of the substrate at the near position.

8 Claims, 12 Drawing Sheets

(51) Int. Cl.
  *H01L 21/687* (2006.01)
  *H01L 21/677* (2006.01)
  *H01L 21/67* (2006.01)

(56) References Cited

U.S. PATENT DOCUMENTS

| | | | |
|---|---|---|---|
| 6,874,515 B2 | 4/2005 | Ishihara et al. | 134/140 |
| 6,929,529 B2* | 8/2005 | Yoshida | B24B 37/04 451/10 |
| 7,270,510 B2* | 9/2007 | Putzi | H01L 21/67173 414/222.01 |
| 7,354,481 B2 | 4/2008 | Okuno et al. | 118/503 |
| 7,918,640 B2 | 4/2011 | Fujii | |
| 8,002,511 B2 | 8/2011 | Kamikawa et al. | 414/416.02 |
| 8,216,391 B2 | 7/2012 | Mokuo | 134/56 R |
| 8,500,915 B2* | 8/2013 | Mitsuyoshi | H01L 21/67781 134/32 |
| 9,050,635 B2* | 6/2015 | Mitsuyoshi | H01L 21/67051 |
| 2002/0192059 A1* | 12/2002 | Foster, Jr. | H01L 21/67132 414/403 |
| 2006/0054082 A1 | 3/2006 | Okuno et al. | 118/50 |
| 2007/0215049 A1* | 9/2007 | Aderhold | H01L 21/67115 118/728 |
| 2008/0175693 A1 | 7/2008 | Fujii | |
| 2008/0199283 A1 | 8/2008 | Mitsuyosh | |
| 2009/0053020 A1 | 2/2009 | Okuno | |
| 2009/0067959 A1* | 3/2009 | Takahashi | B24B 37/345 414/226.01 |
| 2009/0251699 A1* | 10/2009 | George | H01L 21/681 356/401 |
| 2009/0252578 A1 | 10/2009 | Machida | 414/222.01 |
| 2010/0211210 A1 | 8/2010 | Fujii | |
| 2012/0143366 A1 | 6/2012 | Machida | 700/112 |
| 2013/0153116 A1 | 6/2013 | Hirakawa et al. | 156/64 |

FOREIGN PATENT DOCUMENTS

| | | |
|---|---|---|
| JP | 10-321575 | 12/1998 |
| JP | 11-214481 | 8/1999 |
| JP | 2001-043573 | 2/2001 |
| JP | 2002-324828 | 11/2002 |
| JP | 2002-353292 | 12/2002 |
| JP | 2004-241552 A | 8/2004 |
| JP | 2006-503428 | 1/2006 |
| JP | 2006-86222 | 3/2006 |
| JP | 2007-123592 | 5/2007 |
| JP | 2008-198884 | 8/2008 |
| JP | 2008-218906 | 9/2008 |
| JP | 2009-146975 | 7/2009 |
| JP | 4287663 | 7/2009 |
| JP | 2009-252888 | 10/2009 |
| JP | 2012-069906 | 4/2012 |
| TW | 2007-35169 | 9/2007 |
| TW | 2008-43021 | 11/2008 |
| TW | 2009-15470 | 4/2009 |
| WO | WO 2006/137476 A1 | 12/2006 |

OTHER PUBLICATIONS

International Preliminary Report on Patentability (IPRP) issued by the IPEA/EP Patent Office on Dec. 24, 2014 in connection with corresponding application PCT/JP2013/055452.

International Search Report mailed Jun. 4, 2013 in corresponding PCT International Application No. PCT/JP2013/055452.

Taiwanese Office Action issued on Mar. 13, 2015 in connection with Taiwanese Application No. 102134349 with English and Japanese translation of relevant parts.

Japanese Office Action dated Dec. 1, 2015 in corresponding Japanese Patent Application No. 2012-135999, along with English translation of portions relevant to prior-art based rejections.

* cited by examiner

F I G . 2
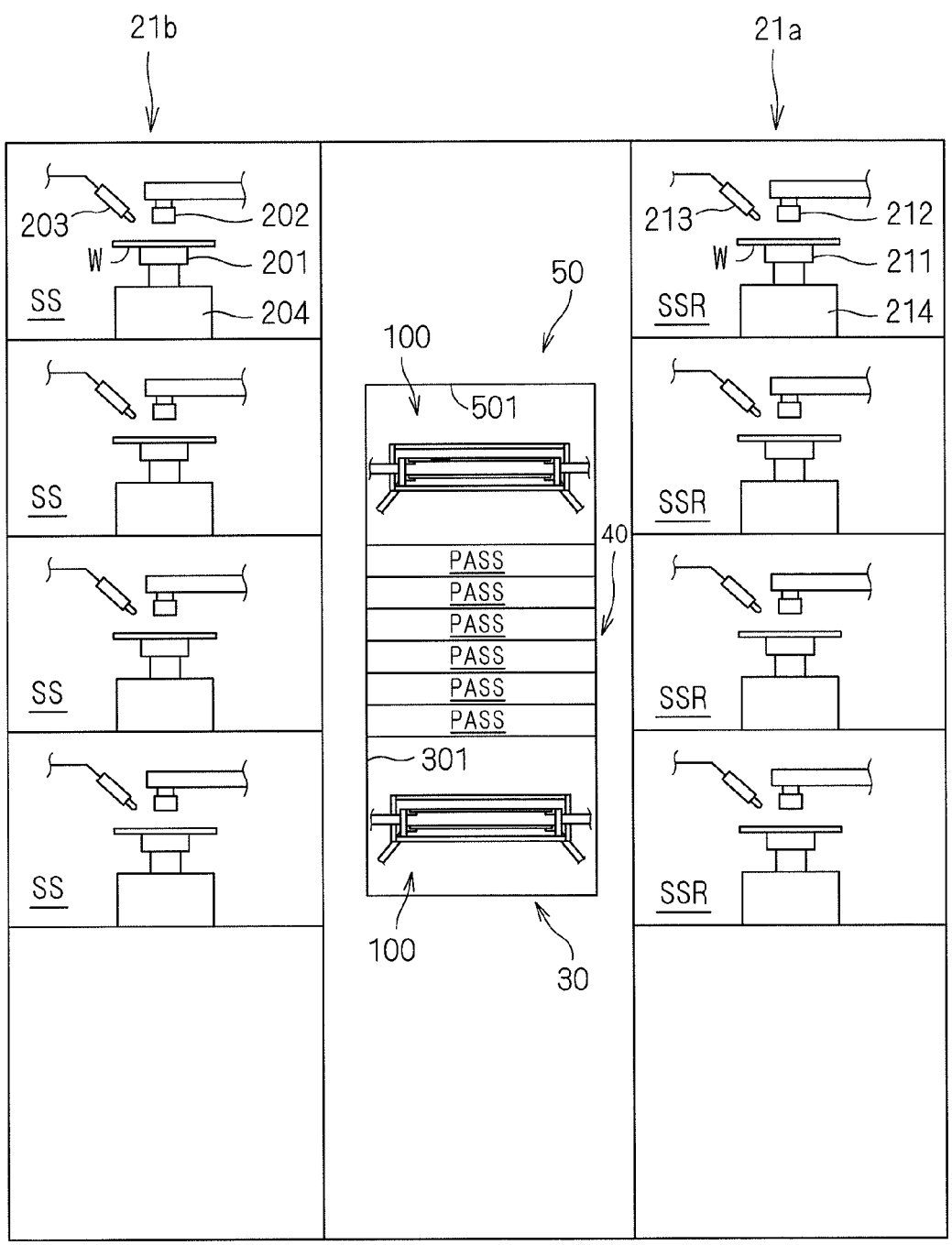

FIG. 8
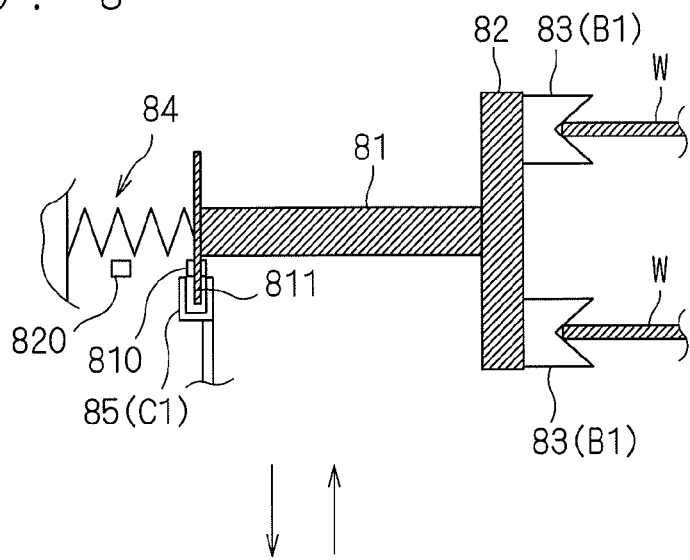
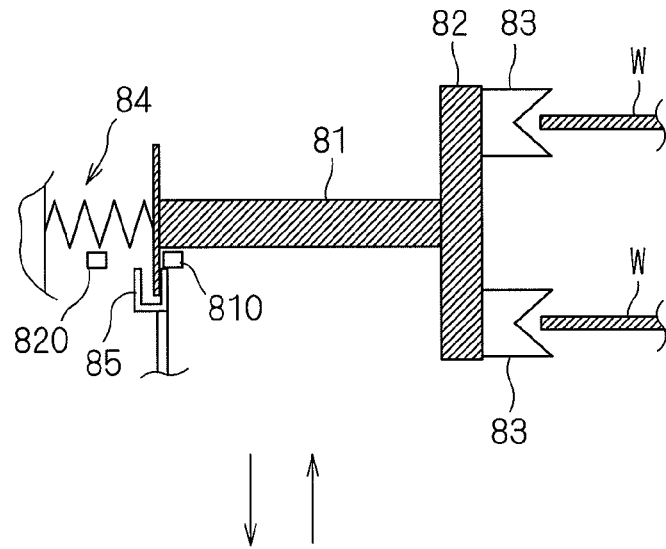
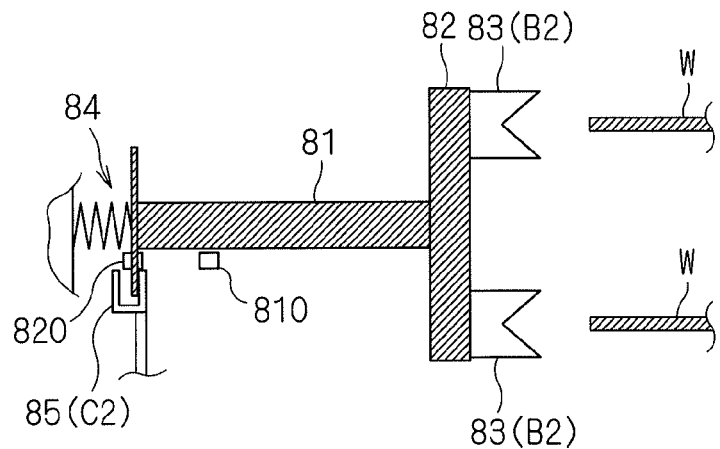

SUBSTRATE INVERTING APPARATUS AND SUBSTRATE PROCESSING APPARATUS

CROSS-REFERENCE TO RELATED APPLICATIONS

The present application is a 35 U.S.C. §§371 national phase conversion of PCT/JP2013/055452, filed Feb. 28, 2013, which claims priority to Japanese Patent Application No. 2012-135999, filed Jun. 15, 2012, the contents of which are incorporated herein by reference. The PCT International Application was published in the Japanese language.

TECHNICAL FIELD

The present invention relates to a technique for applying processing to a plurality of semiconductor substrates, a plurality of glass substrates for liquid crystal display devices, a plurality of glass substrates for plasma displays, a plurality of glass substrates for photo masks, a plurality of substrates for optical disks or the like (simply referred to as "substrates" hereinafter).

BACKGROUND ART

There have been proposed various substrate processing apparatuses where processing is applied to a substrate. For example, substrate processing apparatuses disclosed in Patent Documents 1, 2 are configured such that an indexer cell which stacks non-processed substrates and processed substrates and a cleaning processing cell for performing scrub cleaning processing on substrates are connected to each other by way of a substrate transfer part. A conveyance robot dedicated to respective cells is arranged in the indexer cell and the cleaning processing cell respectively.

In the substrate processing apparatus disclosed in Patent Document 1, to prepare for the case where scrub cleaning processing is applied to a back surface of a substrate, in the inside of a cleaning processing cell, a inverting part which inverts the front and back of the substrate is provided besides a plurality of cleaning processing parts.

As a technique for inverting the front and back of a substrate, for example, Patent Document 2 discloses the constitution where the substrate is clamped between two planer plates (a movable plate and a fixed plate) on which support pins are mounted in an erected manner, and two plates are rotated together with the substrate by 180° thus inverting the front and back of the substrate.

Further, for example, Patent Document 3 discloses the constitution where an edge of a substrate is held by a pair of chucks, and the chucks are rotated together with the substrate which the chucks hold by 180° thus inverting the front and back of the substrate.

Further, for example, Patent Document 4 discloses the constitution which inverts the front and back of a substrate as follows. Firstly, both edge portions along a radial direction of a substrate (that is, a substrate supported by a lower support pin from a lower surface side) are held by clamping members. Then, the lower support pin is moved exactly laterally thus releasing a substrate support state by the lower support pin. Then, clamping members are rotated together with the substrate which the clamping members clamp by 180° thus inverting the front and back of the substrate.

PRIOR ART DOCUMENTS

Patent Documents

Patent Document 1: Japanese Patent Application Laid-Open No. 2009-146975
Patent Document 2: Japanese Patent Application Laid-Open No. 2009-252888
Patent Document 3: Japanese Patent Application Laid-Open No. 10-321575
Patent Document 4: Japanese Patent No. 4287663

SUMMARY OF INVENTION

Problems to be Solved by the Invention

In substrate processing apparatuses, the improvement of throughput has been constantly requested. Under such circumstances, a technique which can invert a plurality of substrates simultaneously has been attracting attention as a technique effectively used for improving the throughput.

However, it is not easy to properly invert a plurality of substrates at a time. For example, according to the technique disclosed in Patent Document 4, there is a possibility that when the lower support pin is retracted in the exactly lateral direction, a lower surface of the substrate and the lower support pin are brought into contact with each other so that a lower surface of the substrate is damaged. Further, according to the technique disclosed in Patent Document 4, the clamping members, upon receiving a drive force from a cylinder, approach an edge portion of the substrate and clamp the substrate. However, for example, when a position or a size of the substrate is slightly deviated from predetermined position and sizes, there may arise a state where the respective clamping members are made to approach too close to side surfaces of the substrate so that the substrate ruptures or a state where the respective clamping members are arranged at positions too away from the side surfaces of the substrate so that the substrate falls.

The present invention has been made in view of the above-mentioned problems, and it is an object of the present invention to provide a technique which can properly invert a plurality of substrates at a time.

Means for Solving the Problems

According to a first aspect of the present invention, there is provided a substrate inverting apparatus for inverting a substrate, which includes: a support mechanism which supports a plurality of substrates in a state where the substrates are stacked vertically in a spaced-apart manner in a horizontal posture; and a clamping and inverting mechanism which clamps the plurality of substrates supported by the support mechanism respectively and inverts the plurality of substrates at a time, wherein the clamping and inverting mechanism comprises: a pair of clamping members which clamps each one of the plurality of substrates from both edge portions; a clamping member drive part which moves the pair of respective clamping members between a near position where a part of the clamping members is arranged close to or is brought into contact with a side surface of the substrate, and a remote position where the clamping members are away from the side surface; and an elastic member which elastically biases the clamping members arranged at the near position toward the side surface of the substrate, the support mechanism comprises: a plurality of support members which support the plurality of respective substrates from a lower surface side thereof; and a support member drive part which moves the plurality of respective support members between a support position where a part of the support member is brought into contact with a lower surface of the substrate, and a standby position where the support member is away from the lower surface, and the support member drive part moves the support member to the standby position from the support position by moving the plurality of respective support members downward while moving the support members away from the center of the substrate as viewed in the vertical direction.

According to a second aspect of the present invention, in the substrate inverting apparatus according to the first aspect, the substrate inverting apparatus further includes a detection part which is provided corresponding to each one of the plurality of respective substrates supported by the support mechanism and detects an abnormality of the corresponding substrate.

According to a third aspect of the present invention, in the substrate inverting apparatus according to the second aspect, the detection part includes a first light emitting part and a first light receiving part, and the first light emitting part and the first light receiving part are arranged to face each other in an opposed manner with the substrate being made to correspond to the detection part sandwiched therebetween as viewed in the vertical direction, and the first light emitting part and the first light receiving part are arranged above and below the substrate separately.

According to a fourth aspect of the present invention, in the substrate inverting apparatus according to the second or third aspect, the detection part includes a second light emitting part and a second light receiving part, and the second light emitting part and the second light receiving part are arranged to face each other in an opposed manner with the substrate being made to correspond to the detection part sandwiched therebetween as viewed in the vertical direction, and the second light emitting part and the second light receiving part are arranged in the same horizontal plane disposed adjacent to a main surface of the substrate.

According to a fifth aspect of the present invention, in the substrate inverting apparatus according to the fourth aspect, the detection part includes a third light emitting part and a third light receiving part, and the third light emitting part and the third light receiving part are arranged to face each other in an opposed manner with the substrate being made to correspond to the detection part sandwiched therebetween as viewed in the vertical direction, and the third light emitting part and the third light receiving part are arranged in the same horizontal plane disposed adjacent to the main surface of the substrate, and a straight line which connects the second light emitting part and the second light receiving part, and a straight line which connects the third light emitting part and the third light receiving part are arranged non-parallel to each other.

According to a sixth aspect of the present invention, in the substrate inverting apparatus according to any one of first to fifth aspects, the clamping and inverting mechanism comprises an opening and closing detection part which detects whether the pair of respective clamping members is at the remote position or at the near position.

According to a seventh aspect of the present invention, there is provided a substrate processing apparatus which includes: the substrate inverting apparatus according to any one of the first to six aspects of the present invention; a front surface cleaning part which cleans a front surface of the substrate; a back surface cleaning part which cleans a back surface of the substrate; and a first conveyance robot which conveys the substrate between the front surface cleaning part, the back surface cleaning part and the substrate inverting apparatus.

According to an eighth aspect of the present invention, the substrate processing apparatus according to the seventh aspect further includes: a processing block where the front surface cleaning part, the back surface cleaning part and the first conveyance robot are arranged; and an indexer block where a second conveyance robot is arranged, and the second conveyance robot transfers a non-processed substrate to the processing block and receives a processed substrate from the processing block, wherein the substrate inverting apparatus is provided at a connecting portion between the indexer block and the processing block, and when either one of the first conveyance robot and the second conveyance robot conveys the substrate into the substrate inverting apparatus, the substrate inverted by the substrate inverting apparatus is delivered by the other conveyance robot.

Effects of the Invention

According to the first aspect, the pair of respective clamping members is moved from a remote position to a near position by the clamping member drive part, and is elastically biased toward the side surfaces of the substrate by the elastic members at the near position. Due to such a constitution, the respective clamping members are elastically biased to the substrate with a required sufficient force and hence, the substrate is not damaged by the pair of clamping members and can be surely clamped by the pair of clamping members. Further, according to the first aspect, the support member is moved downward while moving the support member away from the center of the substrate as viewed in the vertical direction and hence, the support member can be moved to a standby position properly without damaging the substrate by the support member. Accordingly, in the first aspect, a plurality of substrates can be inverted at a time.

According to the second aspect, it is possible to detect abnormalities of the plurality of respective substrates and hence, the plurality of substrates can be inverted safely.

According to the third aspect, the substrate inverting apparatus includes the first light emitting part and the first light receiving part which are arranged to face each other in an opposed manner with the corresponding substrate sandwiched therebetween as viewed in the vertical direction and are arranged separately above and below the substrate. Accordingly, by monitoring an amount of light received by the first light receiving part, when an abnormality occurs with respect to the presence or the non-presence of the corresponding substrate, the abnormality can be immediately detected.

According to the forth aspect, the substrate inverting apparatus includes the second light emitting part and the second light receiving part which are arranged to face each other in an opposed manner with the corresponding substrate sandwiched therebetween as viewed in the vertical direction, and are arranged in the same horizontal plane disposed adjacent to the main surface of the substrate. Accordingly, by monitoring a receiving light amount by the second light receiving part, when an abnormality occurs with respect to the posture of the corresponding substrate, the abnormality can be immediately detected.

According to the fifth aspect, the third light emitting part and the third light receiving part are arranged at positions where the straight line which connects the third light emitting part and the third light receiving part is arranged non-parallel to the straight line which connects the second light emitting part and the second light receiving part. Accordingly, by monitoring both of an amount of light received by the second light receiving part and an amount of light received by the third light receiving part, when an abnormality occurs with respect to a posture of the corresponding substrate, the abnormality can be surely detected.

According to the sixth aspect, the substrate inverting apparatus can detect whether or not the pair of the clamping members clamps the substrate and hence, the plurality of substrates can be safely inverted.

According to the seventh aspect, a plurality of substrates can be properly inverted at a time by the substrate inverting apparatus and hence, a throughput of the substrate processing apparatus can be improved.

According to the eighth aspect, when the substrate is transferred between the second conveyance robot disposed in the indexer block and the first conveyance robot disposed in the processing block, the front and back of the substrate can be inverted. That is, the substrate inverting apparatus also plays a function of a transfer part for the substrate between the first conveyance robot and the second conveyance robot in addition to a function of inverting the substrate. Due to such a constitution, a load of the first conveyance robot is reduced and, at the same time, the number of processing steps in the processing cell can be reduced and hence, lowering of the throughput of the substrate processing apparatus can be effectively suppressed.

Objects, technical features, phases and advantages of the present invention will become more apparent by reference to the following detailed explanation and attached drawings.

BRIEF DESCRIPTION OF DRAWINGS

FIG. 2 is a view of the substrate processing apparatus as viewed from a line A-A in FIG. 1.

FIG. 8 is a view for explaining the manner of operation of the clamping and inverting mechanism.

DESCRIPTION OF EMBODIMENT

Hereinafter, an embodiment of the present invention is described by reference to attached drawings. The embodiment described hereinafter is one example which embodies the present invention, and does not limit the technical scope of the present invention.

Here, in the description made hereinafter, "front surface" of a substrate means a surface on which a pattern (for example, a circuit pattern) is formed out of main surfaces of the substrate, and "back surface" means a surface on a side opposite to the front surface. Further, "upper surface" of the substrate means a surface which faces upward out of the main surfaces of the substrate, and "lower surface" means a surface which faces downward (irrespective of whether the surface being the front surface or the back surface).

<1. Constitution of Substrate Processing Apparatus 1>

Figure 1:
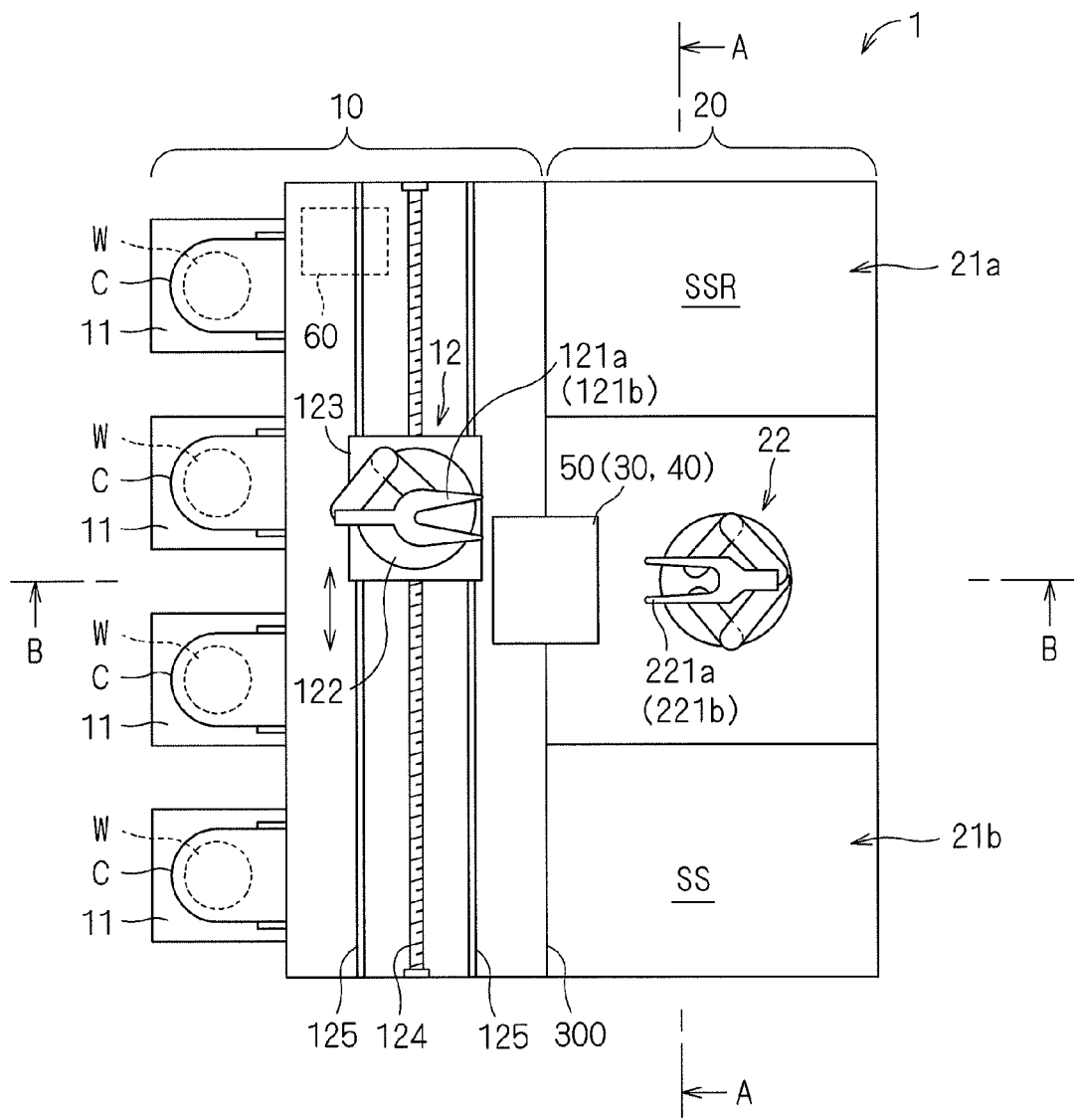
FIG. 1 is a plan view of a substrate processing apparatus according to the present invention.
Figure 3:
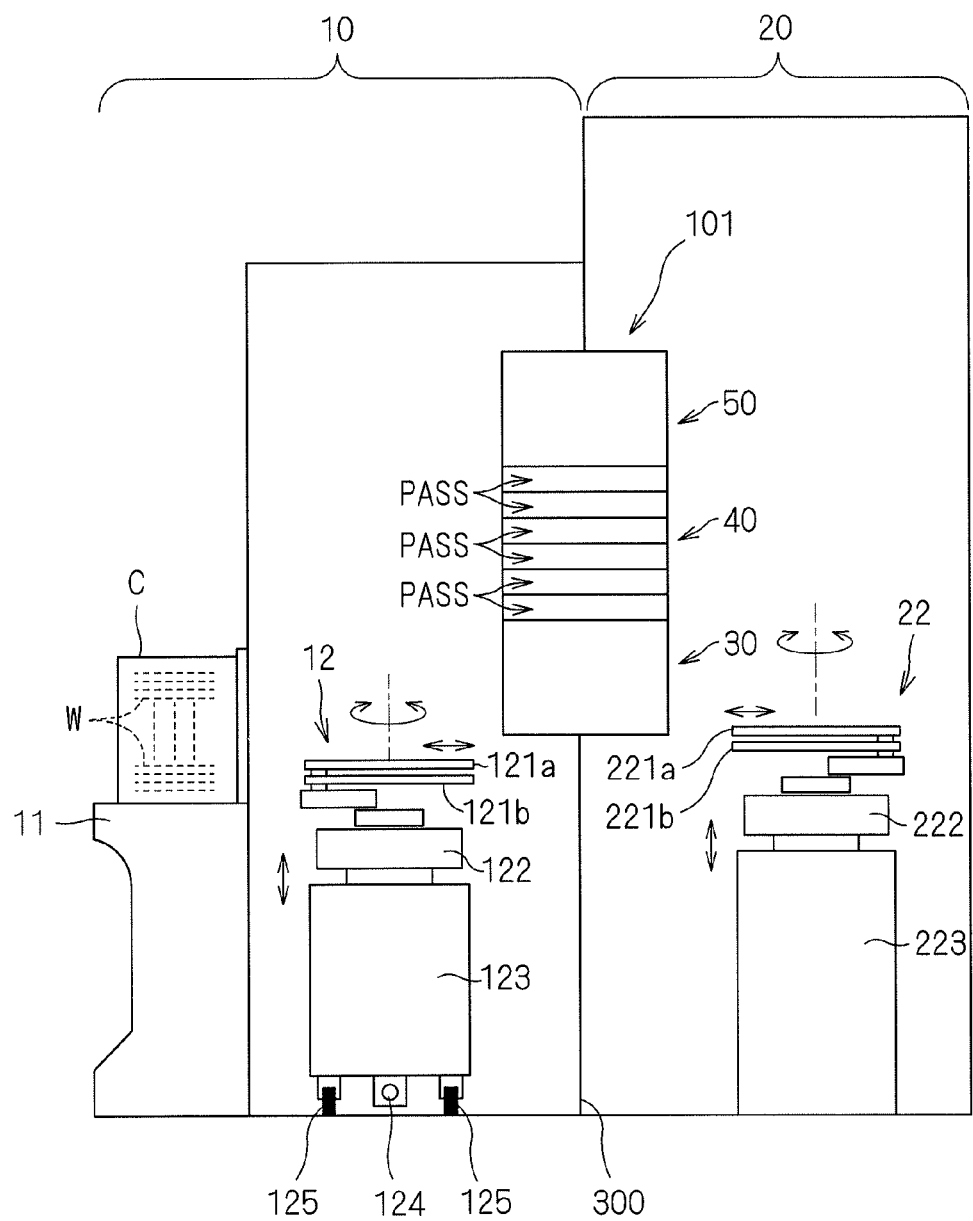
FIG. 3 is a view of the substrate processing apparatus as viewed from a line B-B in FIG. 1.

The constitution of the substrate processing apparatus 1 according to the embodiment is explained by reference to FIG. 1 and FIG. 2. FIG. 1 is a plan view of the substrate processing apparatus 1. FIG. 2 is a view of the substrate processing apparatus 1 as viewed from a line A-A in FIG. 1. FIG. 3 is a view of the substrate processing apparatus 1 as viewed from a line B-B in FIG. 1. Hereinafter, to the respective reference drawings referenced hereinafter, an XYZ orthogonal coordinate system where a Z axis direction is set as the vertical direction and an XY plane is set as a horizontal plane is attached when appropriate.

The substrate processing apparatus 1 is a cleaning apparatus for continuously applying scrub cleaning processing to a plurality of substrates W such as a plurality of semiconductor wafers, and is constituted by arranging two cells (processing blocks), that is, an indexer cell 10 and a cleaning processing cell 20 parallel to each other. The substrate processing apparatus 1 includes respective parts (an inverting and transferring part 30, a placement unit 40, and an inverting part 50) which are disposed between the indexer cell 10 and the cleaning processing cell 20. The substrate processing apparatus 1 further includes a control part 60 which makes operation mechanisms mounted on the indexer cell 10 and the cleaning processing cell 20 executes cleaning processing on the substrates W by controlling the respective operation mechanisms.

<Indexer Cell 10>

The indexer cell 10 is a cell where substrates W (non-processed substrates W) which the indexer cell 10 receives from the outside of the apparatus are transferred to the cleaning processing cell 20 and substrates W (processed substrates W) which the indexer cell 10 receives from the cleaning processing cell 20 are delivered to the outside of the apparatus. The indexer cell 10 includes a plurality of (four in this embodiment) carrier stages 11 on each of which a carrier C is placed, and a transfer robot 12 which takes out a non-processed substrate W from each carrier C and stores a processed substrate W in each carrier C.

A carrier C which stores a non-processed substrate W is conveyed and placed in each carrier stage 11 by an AGV (Automated Guided Vehicle) or the like from the outside of the apparatus. A substrate W with which scrub cleaning processing in the inside of the apparatus is finished is stored in the carrier C placed on the carrier stage 11 again. The carrier C which stores the processed substrate W is delivered to the outside of the apparatus by the AGV or the like. That is, the carrier stage 11 functions as a substrate stacking part which stacks non-processed substrates W and the processed substrates W. Here, as the configuration of the carrier C, an SMIF (Standard Mechanical Inter Face) pod, an OC (open cassette) where stored substrates W are exposed to outside air may be adopted besides an FOUP (front opening unified pod) where the substrate W is stored in a sealed space.

The transfer robot 12 includes two conveyance arms 121a, 121b, an arm stage 122 on which the conveyance arms 121a, 121b are mounted, and a movable table 123.

The movable table 123 is threadedly engaged with a ball screw 124 which extends parallel to the arrangement of the carrier stages 11 (along the Y axis direction) and, at the same time, is mounted on two guide rails 125 in a slidable manner. Due to such a constitution, when the ball screw 124 is rotated by a rotary motor not shown in the drawing, the whole transfer robot 12 including the movable table 123 moves horizontally along the Y axis direction.

The arm stage 122 is mounted on the movable table 123. In the inside of the movable table 123, a motor which rotatively drives the arm stage 122 about an axis extending along the vertical direction (Z axis direction), and a motor which elevatably moves the arm stage 122 along the vertical direction (both motors being not shown in the drawing) are incorporated. The conveyance arms 121a, 121b are arranged on the arm stage 122 at a predetermined pitch in the vertical direction. Both conveyance arms 121a, 121b are formed in a fork shape as viewed in a plan view. Each conveyance arm 121a, 121b supports a lower surface of one substrate W by a fork-shaped portion. The respective conveyance arms 121a, 121b are configured such that the conveyance arms 121a, 121b are movable independently from each other in an extensible and retractable manner along the horizontal direction (in the turning radius direction of the arm stage 122) as an articulated mechanism is retracted and stretched by a driving mechanism (not shown in the drawing) incorporated in the arm stage 122.

Due to such a constitution, the respective conveyance arms 121a, 121b can perform the horizontal movement along the Y axis direction, the elevating movement, the turning operation in the horizontal plane, and the extending and retracting movement along the turning radius direction. The transfer robot 12 conveys the substrate W between the respective parts by making the respective conveyance arms 121a, 121b which support the substrate W by the fork-shaped portions get access to the respective parts (to be more specific, the respective parts of the carriers C placed on the carrier stages 11, the inverting and transferring part 30, and the placement unit 40).

<Cleaning Processing Cell 20>

The cleaning processing cell 20 is a cell for applying scrub cleaning processing to the substrate W, and includes two cleaning processing units 21a, 21b, and a conveyance robot 22 which performs the transfer of the substrate W to the respective cleaning processing units 21a, 21b.

Two cleaning processing units 21a, 21b are arranged to face each other in an opposed manner with the conveyance robot 22 sandwiched therebetween. Out of two cleaning processing units 21a, 21b, the cleaning processing unit 21b on a −Y side of the conveyance robot 22 is constituted by stacking and arranging one or more (four in this embodiment) front surface cleaning processing parts SS in the vertical direction. On the other hand, the other cleaning processing unit 21a (that is, the cleaning processing unit 21a on a +Y side of the conveyance robot 22) is constituted by stacking and arranging one or more (four in this embodiment) back surface cleaning processing parts SSR in the vertical direction.

The front surface cleaning processing part SS applies the scrub cleaning processing to the front surface of the substrate W. To be more specific, for example, the front surface cleaning processing part SS includes: a spin chuck 201 which holds the substrate W having a front surface which faces upward in a horizontal posture and rotates the substrate W about an axis extending along the vertical direction; a cleaning brush 202 which is brought into contact with or is disposed adjacent to the front surface of the substrate W held on the spin chuck 201 thus applying the scrub cleaning to the front surface of the substrate W; a nozzle 203 which discharges a cleaning liquid (for example, pure water) to the front surface of the substrate W; a spin motor 204 which rotatively drives the spin chuck 201; a cup (not shown in the drawing) which surrounds the periphery of the substrate W held on the spin chuck 201 and the like.

The back surface cleaning processing part SSR applies scrub cleaning processing to the back surface of the substrate W. To be more specific, for example, the back surface cleaning processing part SSR includes: a spin chuck 211 which holds the substrate W having back surface which faces upward in a horizontal posture and rotates the substrate W about an axis extending along the vertical direction; a cleaning brush 212 which is brought into contact with or is disposed adjacent to the back surface of the substrate W held on the spin chuck 211 thus applying the scrub cleaning to the back surface of the substrate W; a nozzle 213 which discharges a cleaning liquid (for example, pure water) to the back surface of the substrate W; a spin motor 214 which rotatively drives the spin chuck 211; a cup (not shown in the drawing) which surrounds the periphery of the substrate W held on the spin chuck 211 and the like. The spin chuck 201 used in the front surface cleaning processing part SS which performs the front surface cleaning holds the substrate W from a back surface side and hence, there arises no problem even when the spin chuck 201 is of a vacuum suction type. However, the spin chuck 211 used in the back surface cleaning processing part SSR which performs the back surface cleaning, since the substrate W is to be held from a front surface side, must be of a type which mechanically holds an edge portion of the substrate.

The conveyance robot 22 includes: two conveyance arms 221a, 221b; an arm stage 222 on which the conveyance arms 221a, 221b are mounted; and a base table 223. The base table 223 is fixedly mounted on a frame of the cleaning processing cell 20. Accordingly, the conveyance robot 22 is not configured such that the whole conveyance robot 22 is moved in the horizontal direction.

The arm stage 222 is mounted on the base table 223. In the inside of the base table 223, a motor which rotatively drives the arm stage 222 about an axis extending along the vertical direction (Z axis direction), and a motor which elevatably moves the arm stage 222 along the vertical direction (both motors being not shown in the drawing) are incorporated. The conveyance arms 221a, 221b are arranged on the arm stage 222 at a predetermined pitch in the vertical direction. Both conveyance arms 221a, 221b are formed in a fork shape as viewed in a plan view. Each conveyance arm 221a, 221b supports a lower surface of one substrate W by a fork-shaped portion. The respective conveyance arms 221a, 221b are configured such that the conveyance arms 221a, 221b are movable independently from each other in an extensible and retractable manner along the horizontal direction (in the turning radius direction of the arm stage 222) as an articulated mechanism is retracted and stretched by a driving mechanism (not shown in the drawing) incorporated in the arm stage 222.

Due to such a constitution, the conveyance robot 22 can perform the transfer and the reception of the substrate W between the respective parts individually by making two conveyance arms 221a, 221b respectively get access to the respective parts (to be more specific, the respective parts consisting of the cleaning processing units 21a, 21b, the inverting and transferring part 30, the placement unit 40, and the inverting part 50). As an elevating and lowering drive mechanism of the conveyance robot 22, other mechanisms such as a belt feeding mechanism which uses a pulley and a timing belt may be adopted.

<Inverting and Transferring Part 30>

In the substrate processing apparatus 1, the cleaning processing cell 20 is arranged adjacent to the indexer cell 10, and an atmosphere-shielding partition wall 300 is disposed between the indexer cell 10 and the cleaning processing cell 20. The inverting and transferring part 30 is mounted in the partition wall 300 in a state where the inverting and transferring part 30 penetrates a portion of the partition wall 300. That is, the inverting and transferring part 30 is provided at a connecting portion between the indexer cell 10 and the cleaning processing cell 20.

The inverting and transferring part 30 is interposed between the indexer cell 10 and the cleaning processing cell 20 for transferring a non-processed substrate W to the cleaning processing cell 20 from the indexer cell 10 after inverting a front surface and a back surface of the non-processed substrate W by 180° or for transferring a processed substrate W to the indexer cell 10 from the cleaning processing cell 20 after inverting a front surface and a back surface of the processed substrate W by 180°. That is, the inverting and transferring part 30 has a function of an inverting part for inverting the substrate W as well as a function of a transfer part for transferring a substrate W between the transfer robot 12 and the conveyance robot 22. The constitution of the inverting and transferring part 30 is described later.

<Placement Unit 40>

The placement unit 40 is mounted in the partition wall 300 in a state where the placement unit 40 penetrates a portion of the partition wall 300, and is arranged above the inverting and transferring part 30 in a stacked manner. That is, also the placement unit 40 is provided at the connecting portion between the indexer cell 10 and the cleaning processing cell 20. A gap may be formed between the placement unit 40 and the inverting and transferring part 30.

The placement unit 40 is interposed between the indexer cell 10 and the cleaning processing cell 20 for transferring a non-processed substrate W to the cleaning processing cell 20 from the indexer cell 10 or for transferring a processed substrate W to the indexer cell 10 from the cleaning processing cell 20. In the placement unit 40, a plurality of (for example, six in this embodiment) placement parts PASS each of which supports one substrate W in a horizontal posture are arranged in a stacked manner in the vertical direction. Due to such a constitution, in the placement unit 40, six substrates W can be supported simultaneously in a state where the substrates W are stacked in the vertical direction in a spaced-apart manner in a horizontal posture. Out of six placement parts PASS which the placement unit 40 includes, three placement parts PASS on an upper side are used for the transfer of a processed substrate W from the cleaning processing cell 20 to the indexer cell 10 (so-called a returning placement part). On the other hand, three placement parts PASS on a lower side are used for the transfer of a non-processed substrate W from the indexer cell 10 to the cleaning processing cell 20 (so-called a feeding placement part).

<Inverting Part 50>

The inverting part 50 is mounted on the partition wall 300 such that the inverting part 50 penetrates a portion of the partition wall 300, and is arranged above the placement unit 40 in a stacked manner. That is, the inverting part 50 is also provided at the connecting portion between the indexer cell 10 and the cleaning processing cell 20. However, a gap may be formed between the placement unit 40 and the inverting part 50.

The inverting part 50 is a processing part which inverts a front surface and a back surface of the substrate W by 180°. The inverting part 50 is configured such that a substrate inverting apparatus 100 explained later is housed in a box-shaped casing 501. However, the box-shaped casing 501 is configured to allow only the conveyance robot 22 to get access to the inside of the casing 501. That is, an opening is not formed in a wall portion of the box-shaped casing 501 on an indexer cell 10 side, and an opening (not shown in the drawing) for allowing conveyance arms 221a, 221b of the conveyance robot 22 to get access to the inside of the casing 501 is formed only in a wall portion of the box-shaped casing 501 on a cleaning processing cell 20 side.

<Control Part 60>

The control part 60 controls various operation mechanisms mounted on the substrate processing apparatus 1. The constitution of hardware of the control part 60 is substantially equal to the constitution of an ordinary computer. That is, the control part 60 includes: a CPU which performs various arithmetic processing; a ROM which is a read-only-memory for storing a basic program; a RAM which is a memory for storing data to be read and write; and a magnetic disk for storing a control-use software, data and the like.

<Manner of Operation of Substrate Processing Apparatus 1>

The manner of operation of substrate processing apparatus 1 is explained by reference to FIG. 1 to FIG. 3 again. As described previously, the substrate processing apparatus 1 includes: the front surface cleaning processing part SS which performs the scrub cleaning processing of the front surface of the substrate W; and the back surface cleaning processing part SSR which performs the scrub cleaning processing of the back surface of the substrate W. Due to such a constitution, the substrate processing apparatus 1 can perform cleaning processing of various patterns (for example, cleaning processing in which only the front surface of the substrate W is cleaned, cleaning processing in which only the back surface of the substrate W is cleaned, cleaning processing in which both the front surface and the back surface of the substrate W are cleaned and the like) depending on purposes. A kind of cleaning processing to be performed is determined in accordance with a recipe where the conveyance sequence of the substrate W (the conveyance sequence of the substrate also being referred to as "flow") and processing conditions are described. Hereinafter, the manner of operation of the substrate processing apparatus 1 is explained by taking the case where cleaning processing for cleaning both surfaces of the substrate W is executed.

The carrier C which stores the non-processed substrates W is conveyed into the carrier stage 11 of the indexer cell 10 from the outside of the substrate processing apparatus 1 by an AGV or the like, the transfer robot 12 of the indexer cell 10 takes out two non-processed substrates W from the carrier C by the conveyance arms 121a, 121b, and two substrates W taken out in this manner are conveyed to the inverting and transferring part 30.

In the inverting and transferring part 30 into which two non-processed substrates W are conveyed, the substrate inverting apparatus 100 inverts the front and back of two substrates W so that the respective substrates W are brought into a state where the back surface faces upward. The manner of operation of the substrate inverting apparatus 100 is explained later.

When two substrates W are inverted in the inverting and transferring part 30, the conveyance robot 22 of the cleaning processing cell 20 receives two inverted substrates W (that is, two substrates W whose back surfaces face upward) from the inverting and transferring part 30 by the conveyance arms 221a, 221b, and conveys the respective received substrates W to the back surface cleaning processing part SSR. As described previously, the cleaning processing unit 21b according to this embodiment includes four back surface cleaning processing parts SSR arranged in a stacked manner. The conveyance robot 22 selects two arbitrary back surface cleaning processing parts SSR from four back surface cleaning processing parts SSR, and conveys the substrate W to two selected back surface cleaning processing parts SSR one for each.

The back surface cleaning processing of the substrate W is executed on two respective back surface cleaning processing parts SSR into which the substrates W are conveyed. That is, in the respective back surface cleaning processing part SSR, while holding the substrate W whose back surface faces upward by a spin chuck 211 and rotating the substrate W, a cleaning liquid is supplied to the back surface of the substrate W from a nozzle 213. By bringing a cleaning brush 212 into contact with the back surface of the substrate W or by making the cleaning brush 212 approach the back surface of the substrate W thus allowing the cleaning brush 212 to scan the back surface of the substrate W in the horizontal direction in such a state, scrub cleaning processing is applied to the back surface of the substrate W.

When the back surface cleaning processing of the substrate W is finished in the respective back surface cleaning processing parts SSR, the conveyance robot 22 takes out the substrate W using the conveyance arms 221a, 221b after the back surface cleaning processing from two respective back surface cleaning processing parts SSR sequentially, and conveys two taken-out substrates W to the inverting part 50.

In the inverting part 50 into which two substrates W are conveyed after the back surface cleaning processing, the substrate inverting apparatus 100 inverts the front and back of two substrates W so that the respective substrates W are brought into a state where the front surfaces of the substrates W face upward.

When two substrates W are inverted in the inverting part 50, the conveyance robot 22 receives two inverted substrates W (that is, two substrates W whose front surfaces face upward) from the inverting part 50 by the conveyance arms 221a, 221b, and conveys two respective received substrates W to the front surface cleaning processing part SS. As described previously, the cleaning processing unit 21a according to this embodiment includes four front surface cleaning processing parts SS arranged in a stacked manner. The conveyance robot 22 selects two arbitrary front surface cleaning processing parts SS from four front surface cleaning processing parts SS, and conveys the substrates W to two selected front surface cleaning processing parts SS one for each.

The front surface cleaning processing of the substrate W is executed on two respective front surface cleaning processing parts SS into which the substrates W are conveyed. That is, in the respective front surface cleaning processing parts SS, while holding the substrate W whose front surface faces upward by a spin chuck 201 and rotating the substrate W, a cleaning liquid is supplied to the front surface of the substrate W from a nozzle 203. By bringing a cleaning brush 202 into contact with the front surface of the substrate W or by making the cleaning brush 202 approach the front surface of the substrate W thus allowing the cleaning brush 202 to scan the front surface of the substrate W in the horizontal direction in such a state, scrub cleaning processing is applied to the front surface of the substrate W.

When the front surface cleaning processing applied to the substrate W is finished in the respective front surface cleaning processing parts SS, the conveyance robot 22 takes out the substrate W using the conveyance arms 221a, 221b after the front surface cleaning processing from the respective two front surface cleaning processing parts SS sequentially, and conveys two taken-out substrates W to the placement part PASS.

When the post-processing substrates W are placed on the placement parts PASS, the transfer robot of the indexer cell 10 takes out the post-processing substrates W using the conveyance arms 121a, 121b and stores the post-processing substrates W in the carrier C.

The substrate inverting apparatus 100 which the inverting and transferring part 30 includes and the substrate inverting apparatus 100 which the inverting part 50 includes can, as will become apparent later, properly invert two substrates W at a time. Accordingly, a throughput of the substrate processing apparatus 1 can be improved. Particularly, in the substrate processing apparatus 1, at the time of transferring the substrate W between the transfer robot 12 mounted in the indexer cell 10 and the conveyance robot 22 mounted in the cleaning processing cell 20, the front surface and the back surface of the substrate W can be inverted. That is, the substrate inverting apparatus 10 also has a function of a transfer part for transferring the substrate W between the transfer robot 12 and the conveyance robot 22 in addition to a function of inverting the substrate W. Due to such a constitution, for example, compared to the case where the transfer part and the inverting part are provided separately, a load of the conveyance robot 22 can be reduced and, at the same time, the number of processing steps in the cleaning processing cell 20 can be reduced so that the lowering of the throughput of the substrate processing apparatus 1 can be effectively suppressed.

<3. Inverting and Transferring Part 30>
<3-1. Constitution>

Figure 4:
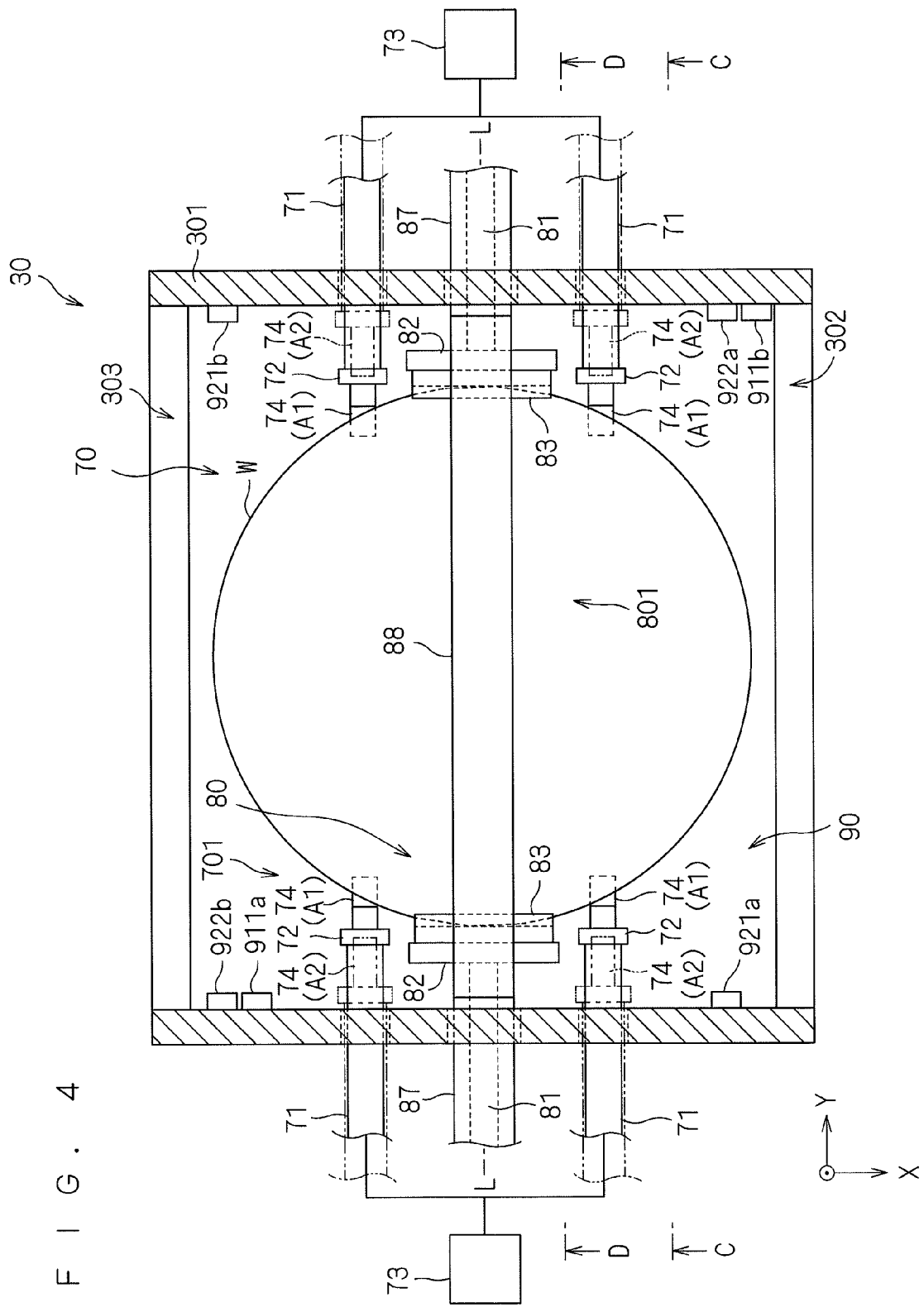
FIG. 4 is a plan view of an inverting and transferring part.
Figure 5:
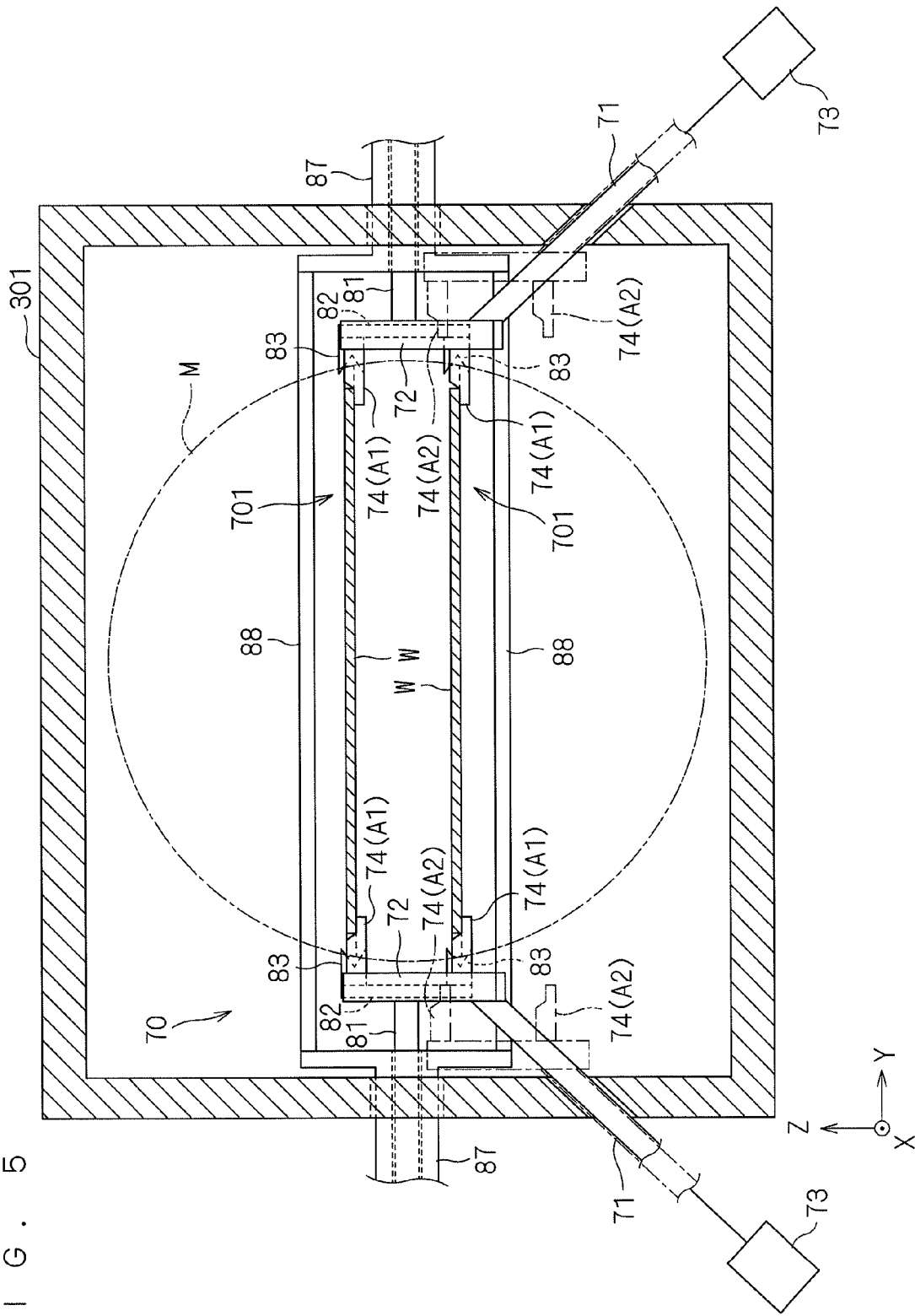
FIG. 5 is a view of the inverting and transferring part as viewed from a line C-C in FIG. 4.
Figure 6:
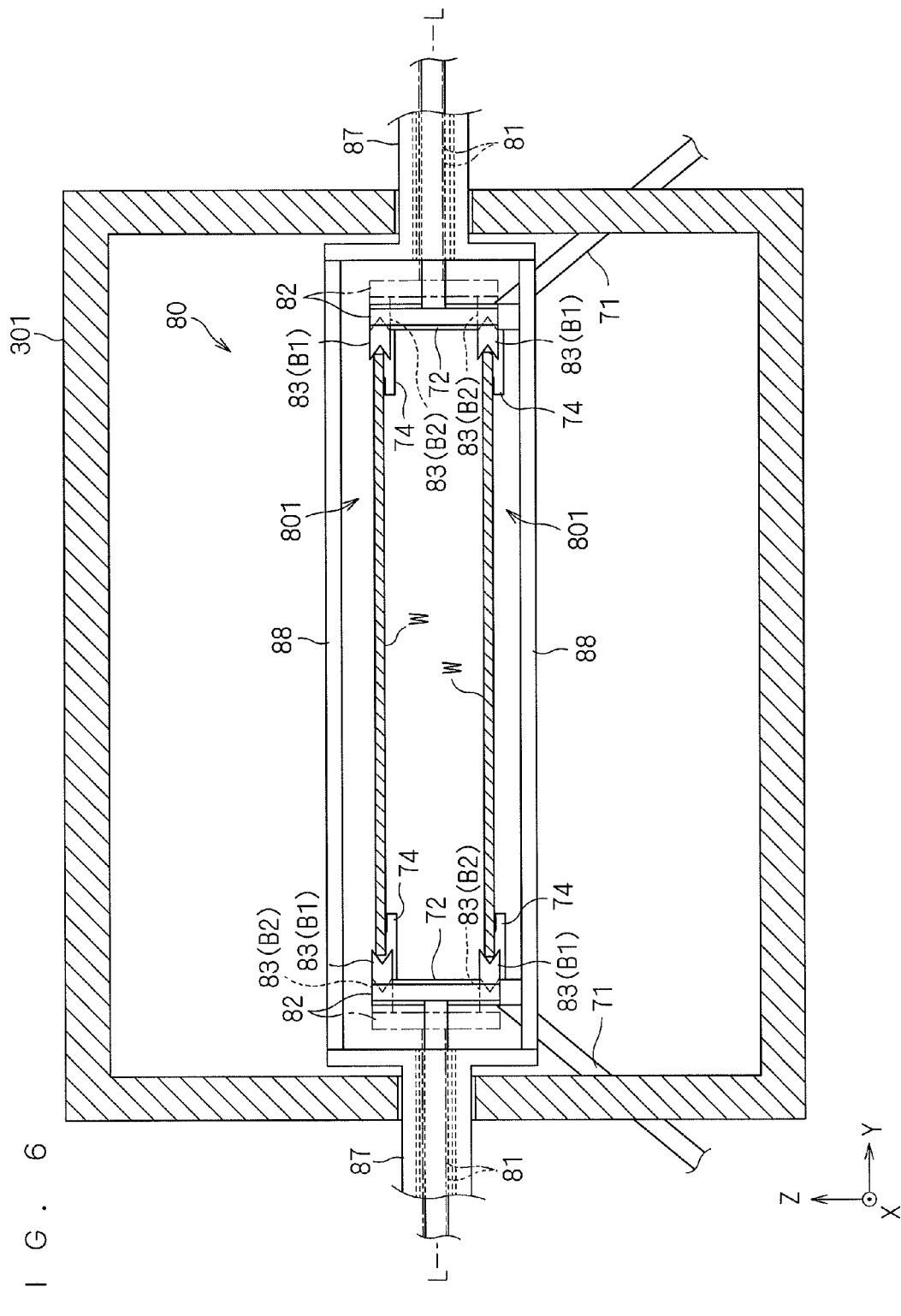
FIG. 6 is a view of the inverting and transferring part as viewed from a line D-D in FIG. 4.

The constitution of the inverting and transferring part 30 is explained by reference to FIG. 4 to FIG. 6. FIG. 4 is a plan view of the inverting and transferring part 30. FIG. 5 is a view of the inverting and transferring part 30 as viewed from a line C-C in FIG. 4. FIG. 6 is a view of the inverting and transferring part 30 as viewed from a line D-D in FIG. 4.

The inverting and transferring part 30 is configured such that a support mechanism 70, a clamping and inverting mechanism 80, detection parts 90 and the like are arranged in the inside of the casing 301. Here, the support mechanism 70 supports a plurality of (two in this embodiment) substrates W stacked in a vertically spaced-apart manner in a horizontal posture. The clamping and inverting mechanism 80 clamps the plurality of respective substrates W supported by the support mechanism 70 and inverts the plurality of substrates W at a time. The detection part 90 is provided to the plurality of respective substrates W. The support mechanism 70, the clamping and inverting mechanism 80 and the detection parts 90 constitute the substrate inverting apparatus 100 which inverts the plurality of (two in this embodiment) substrates W at a time.

Both the transfer robot 12 and the conveyance robot 22 are arranged in the inside of the casing 301 in an accessible manner from the outside. That is, with respect to wall portions of the casing 301, in the wall portion on a cleaning processing cell 20 side (+X side), an opening 302 is formed for allowing the conveyance arms 211a, 221b of the conveyance robot 22 to get access to the inside of the casing 301. With respect to wall portions of the casing 301, in the wall portion on an indexer cell 10 side (−X side), an opening 303 is formed for allowing the conveyance arms 121a, 121b of the transfer robot 12 to get access to the inside of the casing 301. In the explanation made hereinafter, the side (+X side) where the opening 302 is formed for allowing the conveyance arms 221a, 221b of the conveyance robot 22 to get access to the inside of the casing 301 is referred to as "front side", and the side (−X side) where the opening 303 is formed for allowing the conveyance arms 121a, 121b of the transfer robot 12 to get access to the inside of the casing 301 is referred to as "back side". Further, the direction (Y-axis direction) orthogonal to the fore-and-aft direction (X-axis direction) and the vertical direction (Z-axis direction) is referred to as "lateral direction".

<i. Support Mechanism 70>

Two oblique shaft portions 71 are slidably mounted on the left and right side wall portions of the casing 301 respectively in a penetrating manner. Two oblique shaft portions 71 arranged on the respective side wall portions are arranged such that extending directions of the oblique shaft portions 71 are parallel to each other and two oblique shaft portions 71 are spaced-apart from each other in the fore-and-aft direction. In the respective left and right side wall portions, the oblique shaft portions 71 which are arranged on a relatively front side are arranged to face each other in the lateral direction as viewed in the vertical direction, and the oblique shaft portions 71 which are arranged on a relatively back side are also arranged to face each other in the lateral direction as viewed in the vertical direction.

On an upper end portion of each oblique shaft portion 71 which projects to the inside of the casing 301, the supporting column 72 which extends in the vertical direction is arranged. On the other hand, a lower end portion of each oblique shaft portion 71 which projects to the outside of the casing 301 is connected to the cylinder 73. Two oblique shaft portions 71 mounted on the same side wall portions are connected to the same cylinder 73 by way of a connecting rod (not shown in the drawings). That is, the respective lower end portions of the two oblique shaft portions 71 are respectively connected to a portion in the vicinity of a front-side end portion and a portion in the vicinity of a back-side end portion of the connecting rod which extends in the fore-and-aft direction, and the cylinder 73 is connected to the connecting rod. Due to such a constitution, two oblique shaft portions 71 which are connected to the cylinder 73 by way of the connecting rod are synchronously moved by receiving a driving force of the cylinder 73.

On a portion in the vicinity of an upper end and a portion in the vicinity of a lower end of the supporting column 72, a support member 74 which extends in the lateral direction on a horizontal plane is mounted in a cantilever manner. The support member 74 is, to be more specific, an elongated plate-like member which extends from a fixed end thereof mounted on the supporting column 72 to a free end thereof. An upper surface of the support member 74 is formed into a stepped shape where an inclined surface is formed in the middle of extension of the upper surface and an approximately horizontal surface which is relatively lower than a fixed end side is formed on a free end side thereof. The horizontal surface on a free end side constitutes a contact surface which is brought into contact with a lower surface of the substrate W. As will become apparent later, respective contact surfaces of four support members 74 arranged on the same horizontal plane are brought into contact with a lower surface side of the substrate W so that the substrate W is supported in a horizontal posture. It is not always necessary that the contact surface is a horizontal surface and may be a slightly inclined surface which is lowered toward a distal end portion thereof. In the support member 74, the inclined surface which is contiguously formed with the contact surface functions as a position restricting surface which restricts the positions of the edges of the substrate W. That is, by restricting the positions of the edges of the substrate W by the respective inclined surfaces of four support members 74 arranged on the same horizontal plane, the position of the substrate W in a horizontal plane is restricted.

The support members 74 which are arranged on upper ends of four respective supporting columns 72 arranged in the inside of the casing 301 are arranged in the same horizontal plane and constitute one group of support members. The support members 74 which are arranged on lower ends of four respective supporting columns 72 are also arranged in the same horizontal plane, and constitute one group of support members. One substrate W is supported by four support members 74 which constitute one group of support members from a lower surface side so that one substrate W is supported at the predetermined position in a horizontal posture. That is, one group of support members constitutes the support portion 701 which supports one substrate W in a horizontal posture.

In this manner, the support mechanism 70 is provided with two support portions 701 which are arranged in a spaced-apart manner in the vertical direction so that two substrates W can be supported in a state where two substrates W are stacked in a spaced-apart manner in the vertical direction in a horizontal posture.

Two oblique shaft portions 71 which are arranged to face each other in an opposed manner in the lateral direction as viewed in the vertical direction (that is, being arranged to face each other in an opposed manner with a lateral center line of the substrate W supported by the support portion 701 sandwiched therebetween) constitute a pair of oblique shaft portions 71. The pair of respective oblique shaft portions 71 extends in the oblique downward direction (that is, one oblique shaft portion 71 extends in the downward direction while being away from the other oblique shaft portion 71 arranged to face one oblique shaft portion 71 in an opposed manner in the lateral direction) from upper end portions thereof connected to the supporting column 72, and reaches lower end portions thereof connected to the cylinder 73.

The cylinder 73 makes the respective oblique shaft portions 71 slide along the extending direction of the oblique shaft portions 71. That is, the cylinder 73 makes the oblique shaft portions 71 slide in the oblique downward direction along the extending direction of the oblique slide portions 71, and moves the support member 74 from a support position A1 (that is, a position that a contact surface of the support member 74 is brought into contact with a lower surface of the substrate W so that the support member 74 supports the substrate W) to a standby position A2 (that is, a predetermined position where the support member 74 is spaced apart from a lower surface and side surfaces of the substrate W). Due to such a constitution, the support member 74 at the support position A1 is moved in the oblique downward direction (in other words, being moved downward while being away from the lateral center line of the substrate W), that is, away from the center of the substrate W as viewed in the vertical direction)), and is arranged in a standby position A2. That is, the support member 74 disposed at the support position A1 is moved in the direction simultaneously away from both the lower surface and the side surfaces (to be more specific, side surface portions which face the inclined surface of the support member 74 in an opposed manner) of the substrate W, and is arranged at the standby position A2.

The standby position A2 is set at a position outside a periphery of the substrate W as viewed in the vertical direction. Such a standby position A2 is disposed outside a region (inverting region) M where each substrate W inverted by the clamping and inverting mechanism 80 passes. Accordingly, it is possible to surely prevent the support member 74 arranged at the standby position A2 from interfering with the substrate W to be inverted. Further, it is preferable that the standby position A2 is set above the support position of the lower substrate W (the support position of the substrate W supported below the substrate W supported by the support member 74).

The cylinder 73 makes the oblique shaft portion 71 slide in the oblique upward direction along the extending direction of the oblique shaft portion 71 so that the support member 74 is moved to the support position A1 from the standby position A2. That is, the support member 74 at the standby position A2 is moved in the invert direction on the above-mentioned path so that the support member 74 is moved to the support position A1 from the standby position A2.

It is sufficient that the direction that the support member 74 is moved is the direction which is inclined at an angle larger than 0 with respect to the horizontal direction. A specific value of the angle can be determined based on, for example, a spaced-apart distance in the vertical direction between the substrates W supported by the respective support portions 701, and a spaced-apart distance between a periphery of the substrate W and a position at which the support member 74 is brought into contact with the substrate W. In FIG. 4, the respective support members 74 are configured to be away from the center of the substrate W by being moved in the direction along the Y axis as viewed in the vertical direction. However, the respective support members 74 may be configured to be away from the center of the substrate W by being moved along axes extending radially from the center of the substrate W as viewed in the vertical direction.

<ii. Clamping and Inverting Mechanism 80>

Figure 7:
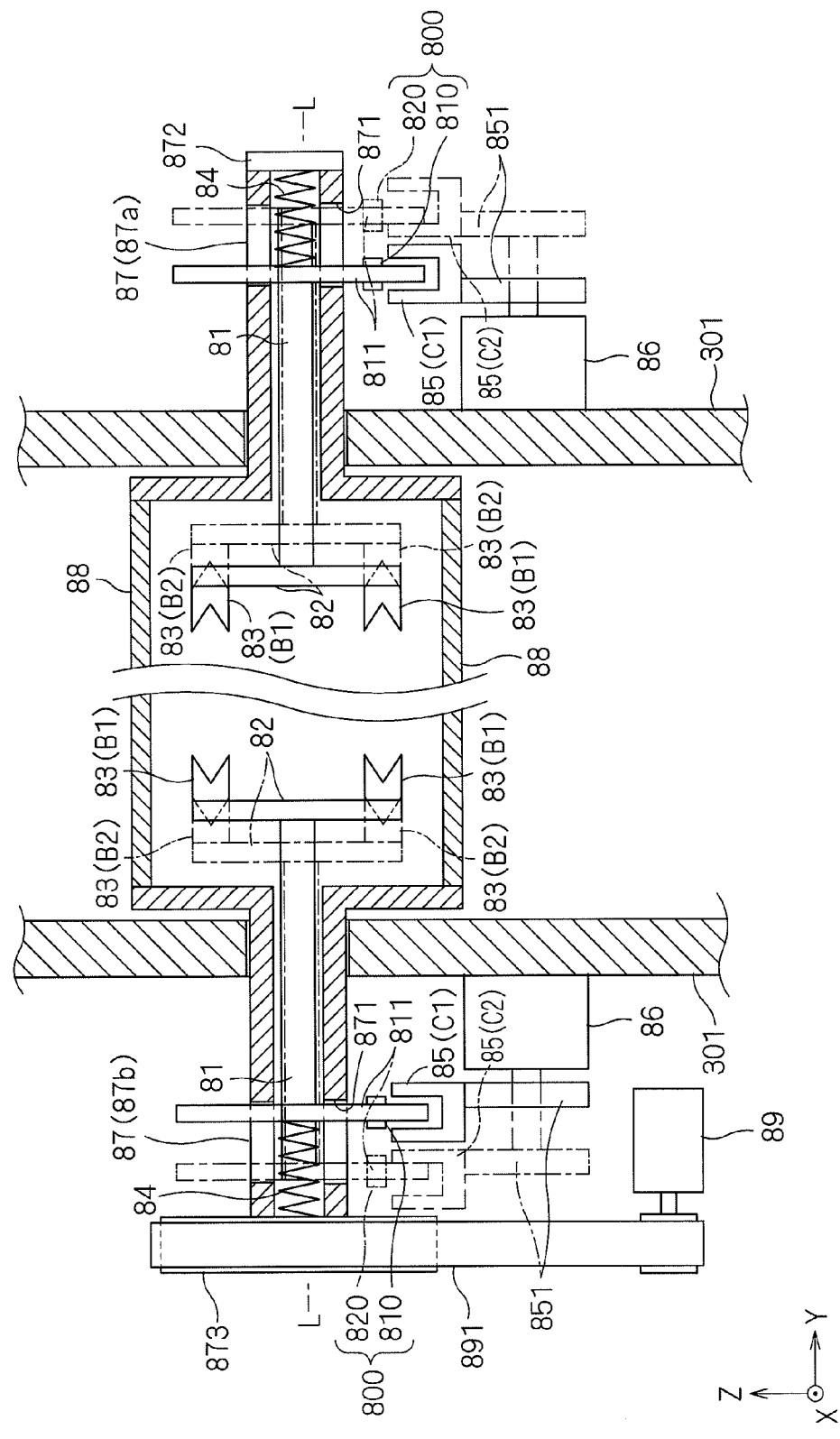
FIG. 7 is a partially-enlarged view showing an essential part of a clamping and inverting mechanism.

The constitution of the clamping and inverting mechanism 80 is explained by reference to FIG. 7 in addition to FIG. 4 to FIG. 6. FIG. 7 is a partially enlarged view showing an essential part of the clamping and inverting mechanism 80.

One slide shaft portion 81 is mounted in left and right side wall portions of the casing 301 respectively in a state where the slide shaft portion 81 slidably penetrates the side wall portion. One slide shaft portion 81 mounted in each side wall portion is arranged between two oblique shaft portions 71 mounted in the side wall portion. The slide shaft portions 81 which are mounted in the left and right side wall portions respectively are arranged to face each other in an opposed manner in the lateral direction as viewed in the vertical direction. The respective slide shaft portions 81 extend in the lateral direction in a horizontal plane. A supporting column 82 which extends in the vertical direction is disposed on end portions of the respective slide shaft portions 81 which project into the inside of the casing 301. The supporting column 82 has a vertically center portion thereof connected to the slide shaft portion 81.

Clamping members 83 which extend in the lateral direction in a horizontal plane are mounted on an upper end and a lower end of the supporting column 82 in a cantilever manner. The clamping member 83 is, more specifically, a member having a tapered surface with a V-shaped cross section in which an edge portion of the substrate W is inserted. The clamping members 83 which are disposed on upper ends of two respective supporting columns 82 arranged in the inside of the casing 301 are arranged in the same horizontal plane. The clamping members 83 which are disposed on lower ends of two respective supporting columns 82 are also arranged in the same horizontal plane. As can be clearly understood later, the pair of clamping members 83 which are disposed in the same horizontal plane clamps the substrate W from both edge portions.

As described above, two slide shaft portions 81 are arranged to face each other in an opposed manner in the lateral direction in the inside of the casing 301. Two respective slide shaft portions 81 extend in the lateral direction in the horizontal plane from one end portions thereof on a side where the supporting column 82 is arranged and reach the other end portions thereof on a side where the side shaft portions 81 project to the outside of the casing 301. The end portion of each slide shaft portion 81 on a side where the slide shaft portion 81 projects to the outside of the casing 301 is brought into contact with an elastic member 84. To be more specific, the elastic member 84 is a coil spring, for example. In a compressed shrunken state, one end portion of the elastic member 84 is brought into contact with an end portion of the slide shaft portion 81, and the other end portion of the elastic member 84 is brought into contact with a pulley 873 (or a bottom plate 872) described later. Accordingly, each slide shaft portion 81 is always biased by the elastic member 84 in the direction that the slide shaft portion 81 is away from the pulley 873 (or the bottom plate 872), that is, in the direction that one slide shaft portion 81 approaches the other slide shaft portion 81 arranged in the lateral direction so as to face one slide shaft portion 81 in an opposed manner.

In such a constitution, the pair of clamping members 83 which is arranged to face each other in an opposed manner in the lateral direction in the same horizontal plane are always brought into a state where the pair of clamping members 83 is elastically biased in the directions that the clamping members 83 approach each other. Since the pair of clamping members 83 are arranged so as to face each other in an opposed manner with the substrate W sandwiched therebetween and the respective clamping members 83 are elastically biased to side surfaces of the substrate W, the substrate W is clamped in a horizontal posture. That is, since one substrate W is clamped by the pair of clamping members 83 which is arranged so as to face each other in an opposed manner in the lateral direction in a state where the substrate W is clamped from both edge portions thereof along the redial direction of the substrate W, the substrate W is clamped in a horizontal posture. Here, "edge portions" of the substrate W indicate a side surface of the substrate W and annular regions on upper and lower surfaces of the substrate W approximately several millimeters from a periphery of the substrate W.

In this manner, in the clamping and inverting mechanism 80, by forming a clamping portion 801 where one pair of clamping members 83 supports one substrate W in a horizontal posture and by providing two clamping portions 801 arranged in a spaced-apart manner in the vertical direction, two substrates W can be clamped in a state where two substrates W are stacked in a spaced-apart manner vertically in a horizontal posture. However, two clamping portions 801 which are arranged in a spaced-apart manner vertically are respectively arranged at the same height as two support portions 701, and the respective clamping portions 801 can clamp the substrates W which are supported by the respective support portions 701.

On an end portion of each slide shaft portion 81 on a side where the slide shaft portion 81 projects to the outside of the casing 301, a projecting portion 811 which projects in a funnel shape from an outer peripheral surface of the slide shaft portion 81 is formed. At least one distal end portion of the projecting portion 811 is inserted into the inside of a groove formed in a gutter portion 85. The gutter portion 85 is a member where the groove opening upward and extending in the fore-and-aft direction is formed, and a width of the groove is set larger than a width of the projecting portion 811. End portions of the groove on front and back sides are also opened. The gutter portion 85 is fixed to a rod of a cylinder 86 by way of a support portion 851. The rod of the cylinder 86 is arranged in a laterally extending manner in a horizontal plane. The projecting portion 811 is formed into a semicircular shape, for example, as viewed in the lateral direction. That is, the projecting portion 811 is formed so as to ensure a state where even after the slide shaft portion 81 is rotated about the axis of rotation L by 180°, at least a portion of a distal end of the projecting portion 811 is inserted into the inside of the groove of the gutter portion 85.

As schematically shown in FIG. 8, the cylinder 86 moves the gutter portion 85 in a reciprocating manner within a predetermined movable range along a moving axis extending in the lateral direction in a horizontal plane. Hereinafter, assume an end portion position on a substrate W side within the movable range of the gutter portion 85 as "closed-side end portion position C1", and the other end portion position within the movable range of the gutter portion 85 as "open-side end portion position C2".

When the cylinder 86 moves the gutter portion 85 in the closed-side end portion position C1 in the direction away from the substrate W, the projecting portion 811 is brought into a state where the projecting portion 811 is caught by the gutter portion 85 so that the slide shaft portion 81 is made to slide in the direction away from the substrate W together with the gutter portion 85 (the flow from an upper stage to a lower stage in FIG. 8). Due to such an operation, the clamping member 83 which is elastically biased to the side surface of the substrate W (that is, the clamping member at the clamping position B1) is moved away from the side surface of the substrate W, is moved in the direction away from a lateral center line of the substrate W (that is, in the direction away from the center of the substrate W) in a horizontal plane, and is arranged at a remote position B2 spaced apart from the side surface of the substrate W. That is, the cylinder 86 moves the gutter portion 85 to the open-side end portion position C2 from the closed-side end portion position C1 so that the clamping member 83 is moved to the remote position B2 from the clamping position B1.

On the other hand, when the cylinder 86 moves the gutter portion 85 at the open-side end portion position C2 in the direction that the gutter portion 85 is made to approach the substrate W, the slide shaft portion 81 is made to slide in the direction that the slide shaft portion 81 approaches the substrate W together with the gutter portion 85 (the flow from a lower stage to an upper stage in FIG. 8). Due to such an operation, the clamping member 83 at the remote position B2 is moved in the direction that the clamping member 83 approaches the lateral center line of the substrate W (that is, in the direction that the clamping member 83 approaches the center of the substrate W) in a horizontal plane. In a state where the cylinder 86 moves the gutter portion 85 to the closed-side end portion position C1, the projecting portion 811 is brought into a state where the projecting portion 811 is spaced-apart from a groove-side wall portion of the gutter portion 85 (preferably a state where the projecting portion 811 is arranged at the approximately center in the groove of the gutter portion 85), that is, a state where the projecting portion 811 does not receive a force from the gutter portion 85. Accordingly, in a state where the gutter portion 85 is arranged at the closed-side end portion position C1, the slide shaft portion 81 is arranged at a position B1 where the clamping member 83 is elastically biased to the side surface of the substrate W with a predetermined pressure by the elastic member 84 (that is, clamping position).

That is, during the moving operation where the cylinder 86 moves the gutter portion 85 from the open-side end portion position C2 to the closed-side end portion position C1, the clamping member 83 is made to approach the substrate W in a state where the clamping member 83 is supported by the cylinder 86 while receiving an elastic biasing force from the elastic member 84 up to a middle stage of the moving operation, and the clamping member 83 is moved to the final clamping position B1 by receiving an elastic biasing force from the elastic member 84 from the middle stage of the moving operation. To be more specific, the clamping member 83 is moved to a near position (that is, a predetermined position where the clamping member 83 approaches or is brought into contact with the side surface of the substrate W) from a remote position B2 by receiving a drive force of the cylinder 86, and, thereafter, the clamping member 83 is further moved to the clamping position B1 from the near position and is elastically biased to the side surface of the substrate W with a predetermined pressure only by an elastic biasing force from the elastic member 84 without using the drive force of the cylinder 86. As described previously, by arranging the pair of clamping members 83 at the clamping position B1 respectively, the substrate W is brought into a state where the substrate W is clamped by the pair of clamping members 83 from both end portions.

Due to such a constitution, the respective clamping members 83 can be elastically biased to the substrate W with a required sufficient force and hence, the substrate W can be surely clamped by the clamping portions 801 without damaging the substrate W. For example, to consider a case where the substrate W is clamped by the respective clamping members only by driving the cylinders without providing elastic members, stop positions of the clamping members are fixed unequivocally. Accordingly, in the case where a position or a size of the substrate W is slightly deviated from a predetermined position or size of the substrate W or the like, there is a possibility that the respective clamping members are made to approach too close to the side surfaces of the substrate W and hence, the substrate W ruptures or a possibility that the respective clamping members are arranged at positions too away from the side surfaces of the substrate W and hence, the substrate W falls. However, according to the above-mentioned constitution, such possibilities minimally occur.

Here, open/close detection parts 800 which detect a positional state of the pair of clamping members 83 are provided to the clamping and inverting mechanism 80. The open/close detection part 800 is, for example, constituted of a pair of optical sensors 810, 820. One sensor (closed-side sensor) 810 is arranged in the vicinity of the closed-side end portion position C1, and detects the projecting portion 811 which is inserted into the inside of the groove of the gutter portion 85 arranged at the closed-side end portion position C1. The other sensor (open-side sensor) 820 is arranged in the vicinity of the open-side end portion position C2, and detects the projecting portion 811 which is inserted into the inside of the groove of the gutter portion 85 arranged at the open-side end portion position C2. As described previously, a width of the groove of the gutter portion 85 is set larger than a width of the projecting portion 811 and hence, the projecting portion 811 can take an arbitrary position within the width of the groove. Accordingly, it is desirable that the respective sensors 810, 820 have detection ranges approximately equal to a groove width of the gutter portion 85 in the lateral direction.

Due to such a constitution, when the gutter portion 85 is moved to the closed-side end portion position C1, the closed-side sensor 810 detects the projecting portion 811 (an upper stage in FIG. 8). That is, when the closed-side sensor 810 detects the projecting portion 811, it is determined that each clamping member 83 is arranged at the near position and, further, the clamping member 83 is arranged at the clamping position B1 by the elastic member 84. On the other hand, when the gutter portion 85 is moved to the open-side end portion position C2, the open-side sensor 820 detects the projecting portion 811 (a lower stage in FIG. 8). That is, when the open-side sensor 820 detects the projecting portion 811, it is determined that each clamping member 83 is arranged at the remote position B2. By detecting whether or not the pair of clamping members 83 clamps the substrate W by the open/close detection parts 800, it is possible to safely invert a plurality of substrates W in the substrate inverting apparatus 100.

The pair of respective slide shaft portions 81 are mounted on the respective side wall portions of the casing 301 in a penetrating manner in a state where the slide shaft portions 81 are inserted into the inside of the hollow rotary shaft portions 87. That is, one rotary shaft portion 87 is mounted on the respective left and right side wall portions of the casing 301 in a penetrating manner and in a rotatable manner, and the slide shaft portion 81 is inserted into the inside of the rotary shaft portion 87 in a slidable manner. However, as described previously, the projecting portion 811 is formed on the end portion of the slide shaft portion 81, and a pass-through opening 871 which allows the projecting portion 811 to pass therethrough is formed in the rotary shaft portion 87. The pass-through opening 871 is formed into a shape having a sufficient length in the lateral direction such that the pass-through opening 871 does not obstruct the movement of the projecting portion 811 in the lateral direction brought about by the sliding of the slide shaft portion 81.

The rotary shaft portion 87 and the slide shaft portion 81 which is inserted into the inside of the rotary shaft portion 87 are configured such that the slide shaft portion 81 cannot be rotated in the inside of the rotary shaft portion 87 about an axis (a central line along the extending direction) by making, for example, an end surface of the pass-through opening 871 (an end surface of the rotary shaft portion 87 in the circumferential direction) catch an end surface of the projecting portion 811 (an end surface of the slide shaft portion 81 in the circumferential direction). Accordingly, when the rotary shaft portion 87 is rotated about the axis (the axis of rotation L), the slide shaft portion 81 is also rotated about the axis of rotation L.

As viewed in the vertical direction, the pair of rotary shaft portions 87 which are arranged so as to face each other in an opposed manner in the lateral direction respectively extends in the lateral direction in a horizontal plane, wherein one end of the rotary shaft portion 87 projects into the inside of the casing 301 and the other end of the rotary shaft portion 87 projects to the outside of the casing 301 respectively. The pair of rotary shaft portions 87 is connected to each other on a side where the rotary shaft portions 87 project to the inside of the casing 301 such that one rotary shaft portion 87 is connected to the other rotary shaft portion 87 by way of a pair of auxiliary bars 88. The pair of auxiliary bars 88 is arranged in a separated manner on an upper side and a lower side of two substrates W which are supported by the support mechanism 70, and the respective auxiliary bars 88 are arranged in the laterally extending manner in a horizontal plane.

Out of the pair of rotary shaft portions 87, on an end portion of one rotary shaft portion (the rotary shaft portion on a +Y side in the example shown in the drawing) 87a which projects to the outside of the casing 301, a bottom plate 872 which closes a hollow portion of the rotary shaft portion 87a is mounted. As described previously, the elastic member 84 is arranged between the slide shaft portion 81 which is made to pass through the hollow portion of the rotary shaft portion 87a and the bottom plate 872 which closes the hollow portion.

Out of the pair of rotary shaft portions 87, on an end portion of the other rotary shaft portion (the rotary shaft portion on a −Y side in the example shown in the drawing) 87b which projects to the outside of the casing 301, a pulley 873 is mounted such that the pulley 873 closes a hollow portion of the rotary shaft portion 87b. As described previously, the elastic member 84 is arranged between the slide shaft portion 81 which is made to pass through the hollow portion of the rotary shaft portion 87b and the pulley 873 which closes the hollow portion.

The pulley 873 is arranged such that the center of rotation of the pulley 873 is aligned with an axis of rotation L of the rotary shaft portion 87. A motor 89 is arranged in the vicinity of the pulley 873, and a belt 891 which transmits a drive force of the motor 89 to the pulley 873 extend between and is wound around the pulley 873 and the motor 89. Due to such a constitution, when the motor 89 is rotated, a rotational force of the motor 89 is transmitted to the pulley 873 by way of the belt 891 so that the pulley 873 is rotated whereby the rotary shaft portion 87b is rotated about the axis (axis of rotation) L of the rotary shaft portion 87b.

As described previously, the pair of rotary shaft portions 87a, 87b are connected to each other by way of the pair of auxiliary bars 88. Accordingly, when one rotary shaft portion 87b is rotated about the axis of rotation L, the other rotary shaft portion 87a is also rotated about the axis (the axis of rotation) L synchronously with the rotation of one rotary shaft portion 87b. That is, a rotational drive force of the motor 89 connected to one rotary shaft portion 87b is also transmitted to the other rotary shaft portion 87a.

As described previously, the respective slide shaft portions 81 cannot be rotated in the inside of the rotary shaft portions 87a, 87b. Accordingly, when the rotary shaft portions 87a, 87b are rotated about the axis of rotation L by 180°, the respective slide shaft portions 81 are also rotated about the axis of rotation L by 180°. As a result, the supporting columns 82 which are connected to the respective slide shaft portions 81 are rotated about connecting portions with the slide shaft portions 81 (that is, the center portions of the supporting columns 82 in the extending direction) by 180° in a vertical plane. Due to such a constitution, two substrates W which are clamped by the respective clamping members 83 arranged on the respective supporting columns 82 are inverted by 180°. In this manner, in the clamping and inverting mechanism 80, two substrates W which are clamped by two clamping portions 801 vertically arranged in a spaced-apart manner can be inverted at a time.

<iii. Detection Part 90>

Figure 9:
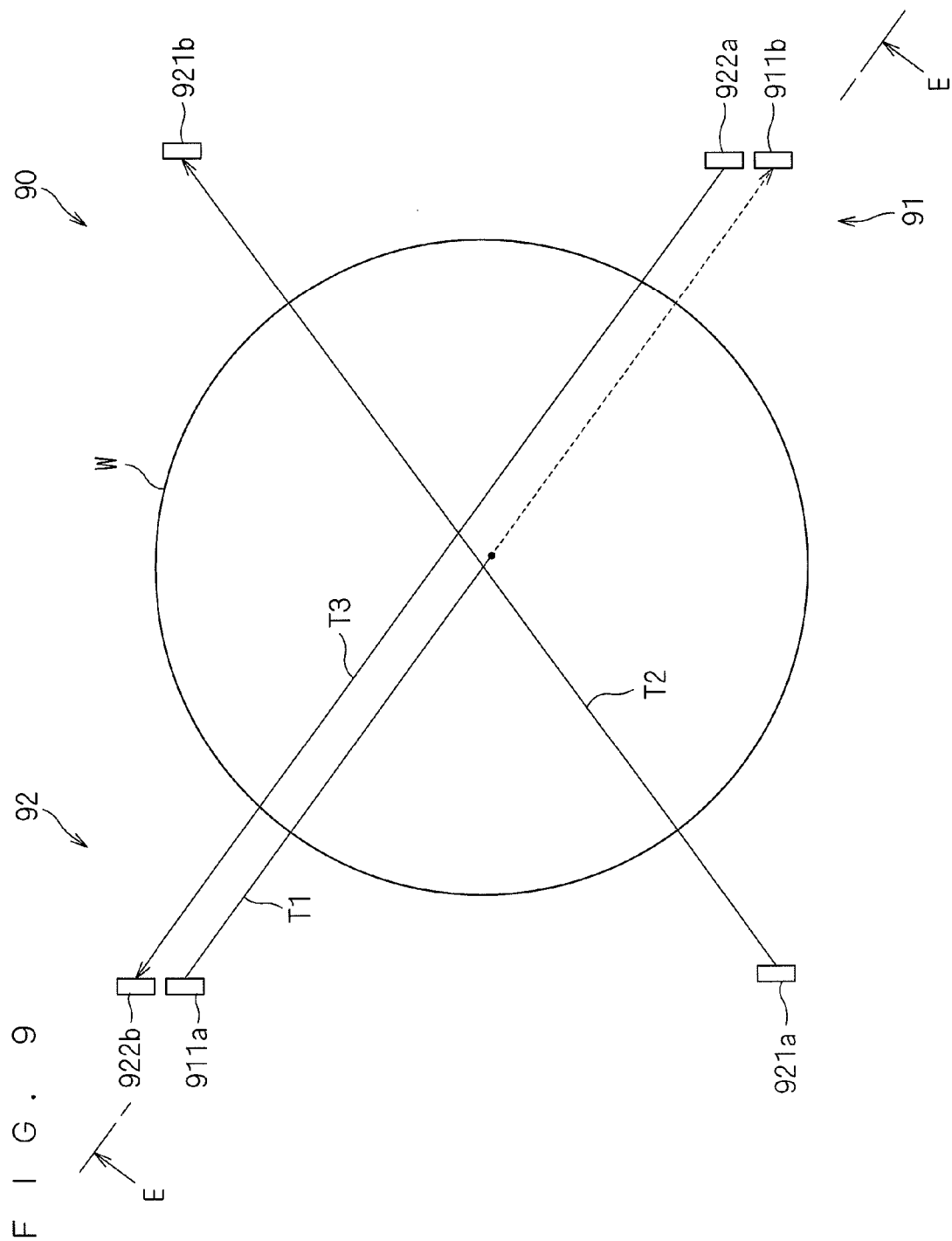
FIG. 9 is a schematic view for explaining a detection part.
Figure 10:
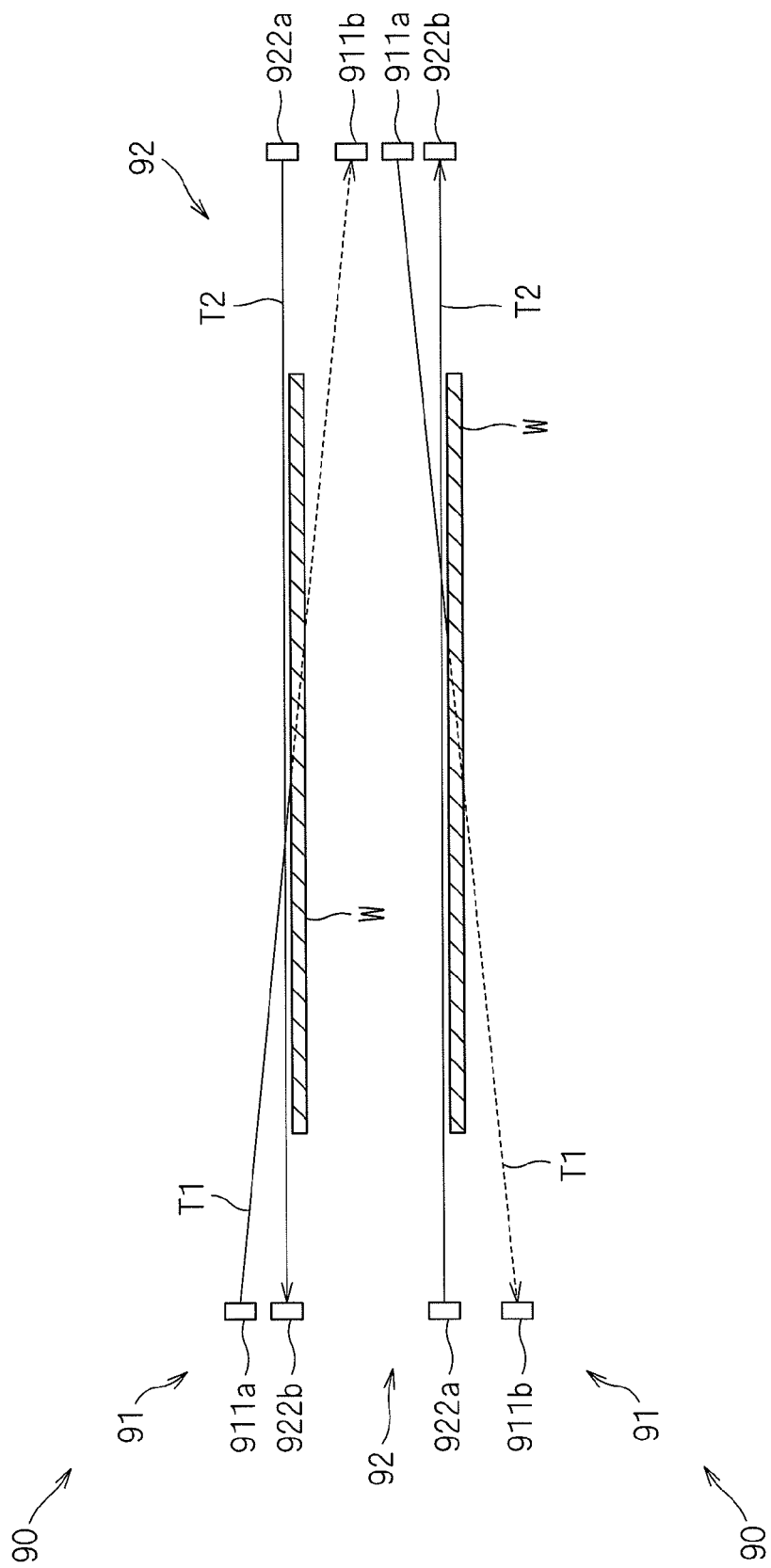
FIG. 10 is a view as viewed from a line E-E in FIG. 9.

The substrate inverting apparatus 100 includes a detection part 90 which is provided corresponding to each one of two substrates W which are supported by the support mechanism 70, and detects an abnormality in the corresponding substrate W. The constitution of the detection part 90 is explained also by reference to FIG. 9 and FIG. 10 in addition to FIG. 4. FIG. 9 is a schematic view for explaining the detection part 90, and schematically shows the relative positional relationship of the detection part 90 with respect to the substrate W supported by the support portion 701. FIG. 10 is a view as viewed from a line E-E in FIG. 9.

As described previously, the detection part 90 adopts one substrate W as an object to be detected, and detects an abnormality in the substrate W which constitutes the object to be detected. That is, one detection part 90 is provided corresponding to one support portion 701 on a one-to-one basis, and each detection part 90 detects an abnormality in the substrate W which becomes an object to be supported by the support portion 701. In the explanation made hereinafter, the substrates W which becomes an object to be detected by the detection part 90 is also referred to as "object substrate W". As described previously, in the substrate inverting apparatus 100, the support mechanism 70 includes two support portions 701 and hence, the substrate inverting apparatus 100 also includes two detection parts 90. These two detection parts 90 have the same constitution.

The detection part 90 includes a presence/non-presence detection part 91 which detects the presence or the non-presence of the object substrate W, and a posture abnormality detection part 92 which detects an abnormality in a posture of the object substrate W.

The presence/non-presence detection part 91 includes: a first light emitting part 911a constituted of a light source which emits, for example, a laser beam; and a first light receiving part 911b constituted of a line sensor, for example. The first light emitting part 911a and the first light receiving part 911b are respectively arranged at predetermined positions on an inner wall of the casing 301. However, the first light emitting part 911a and the first light receiving part 911b are arranged to face each other in an opposed manner with the object substrate W sandwiched therebetween as viewed in the vertical direction and are arranged separately above and below the object substrate W. That is, the first light emitting part 911a and the first light receiving part 911b are arranged in the relative positional relationship such that a straight line T1 which connects the respective parts penetrates the object substrate W. It is particularly preferable that the first light emitting part 911a and the first light receiving part 911b are arranged in the relative positional relationship such that the straight line T1 which connects the respective parts penetrates an area in the vicinity of the center of the object substrate W in a state where the object substrate W is normally arranged.

With such a constitution, when the object substrate W is not present, a light emitted from the first light emitting part 911a is detected by the first light receiving part 911b. On the other hand, when the object substrate W is present, a light emitted from the first light emitting part 911a is not detected by the first light receiving part 911b. Accordingly, it is determined that the object substrate W is not present when an amount of light received by the first light receiving part 911b exceeds a predetermined value. By monitoring an amount of light received by the first light receiving part 911b in this manner, when an abnormality in the presence or non-presence of an object substrate W (that is, an abnormality that an object substrate W which is to be supported by the support portion 701 (or the clamping portion 801) is not present at a predetermined position at an actual operation or an abnormality that an object substrate W which should not be supported by the support portion 701 (or the clamping portion 801) is present) occurs, this abnormality can be immediately detected.

The posture abnormality detection part 92 includes two light emitting parts (second light emitting part 921a and third light emitting part 922a) and two light receiving parts (second light receiving part 921b and third light receiving part 922b). The light emitting parts 921a, 922a are respectively constituted of a light source which emits a laser beam. Further, the light receiving parts 921b, 922b are respectively constituted of a line sensor, for example.

These parts 921a, 922a, 921b, 922b are respectively arranged at predetermined positions on the inner wall of the casing 301. However, the second light emitting part 921a and the second light receiving part 921b are arranged so as to face each other in an opposed manner with an object substrate W sandwiched therebetween as viewed in the vertical direction and are arranged in the same horizontal plane. In the same manner, the third light emitting part 922a and the third light receiving part 922b are arranged so as to face each other in an opposed manner with an object substrate W sandwiched therebetween as viewed in the vertical direction and are arranged in the same horizontal plane. Accordingly, both of a straight line T2 which connects the second light emitting part 921a and the second light receiving part 921b to each other and a straight line T3 which connects the third light emitting part 922a and the third light receiving part 922b to each other extend parallel to a main surface of the object substrate W which is supported in a horizontal posture. However, the horizontal plane on which the respective parts 921a, 922a, 921b, 922b are arranged is set as a plane disposed adjacent to the main surface (that is, a plane away from the main surface by a small amount of distance). The smaller an amount of distance between the horizontal plane and the main surface, the finer inclination of the object substrate W which the detection part can detect becomes. Accordingly, an amount of distance between the horizontal plane and the main surface can be determined corresponding to an allowable inclination angle of the object substrate W. The horizontal plane on which the second light emitting part 921a and the second light receiving part 921b are arranged and the horizontal plane on which the third light emitting part 922a and the third light receiving part 922b are arranged may be the same horizontal plane.

However, the respective parts 921a, 922a, 921b, 922b are arranged such that the straight line T2 which connects the second light emitting part 921a and the second light receiving part 921b to each other and the straight line T3 which connects the third light emitting part 922a and the third light receiving part 922b to each other become non parallel to each other. It is preferable that these parts 921a, 922a, 921b, 922b are arranged in a relative positional relationship where an intersecting point between the straight line T2 and the straight line T3 is disposed in the vicinity of an area just above the center position of the object substrate W. It is also preferable that the parts 921a, 922a, 921b, 922b are arranged in a relative positional relationship where the straight line T2 and the straight line T3 respectively agree with the straight line which connects the support members 74 arranged diagonally out of four support members 74 which constitute the support portion 701 (or are arranged close to the straight line which connects the support members 74).

With such a constitution, when the object substrate W is in a horizontal posture, a light from the second light emitting part 921a is detected by the second light receiving part 921b. On the other hand, when the object substrate W is in a posture inclined from the horizontal posture (excluding a case where the object substrate W is in an inclined posture by rotating about an axis extending parallel to the straight line T2), a light from the second light emitting part 921a is not detected by the second light receiving part 921b. In the same manner, when the object substrate W is in a horizontal posture, a light from the third light emitting part 922a is detected by the third light receiving part 922b. On the other hand, when the object substrate W is in a posture inclined from the horizontal posture (excluding a posture where the object substrate W is in an inclined posture by rotating about an axis extending parallel to the straight line T3), a light from the third light emitting part 922a is not detected by the third light receiving part 922b. Accordingly, when at least one of an amount of light received by the second light receiving part 921b and an amount of light received by the third light receiving part 922b becomes smaller than a predetermined amount, it is determined that the object substrate W is not supported in a horizontal posture, that is, an abnormality is present in the posture of the object substrate W. In this manner, by monitoring an amount of light received by the second light receiving part 921b and an amount of light received by the third light receiving part 922b, when there occurs an abnormality in the posture of the object substrate W (that is, an abnormality where an object substrate W which is to be supported in a horizontal posture by the support part 701 (or clamping part 801) assumes an inclined posture, such an abnormality can be surely detected.

<3-2. Manner of Operation of Substrate Inverting Apparatus 100>

Figure 11:
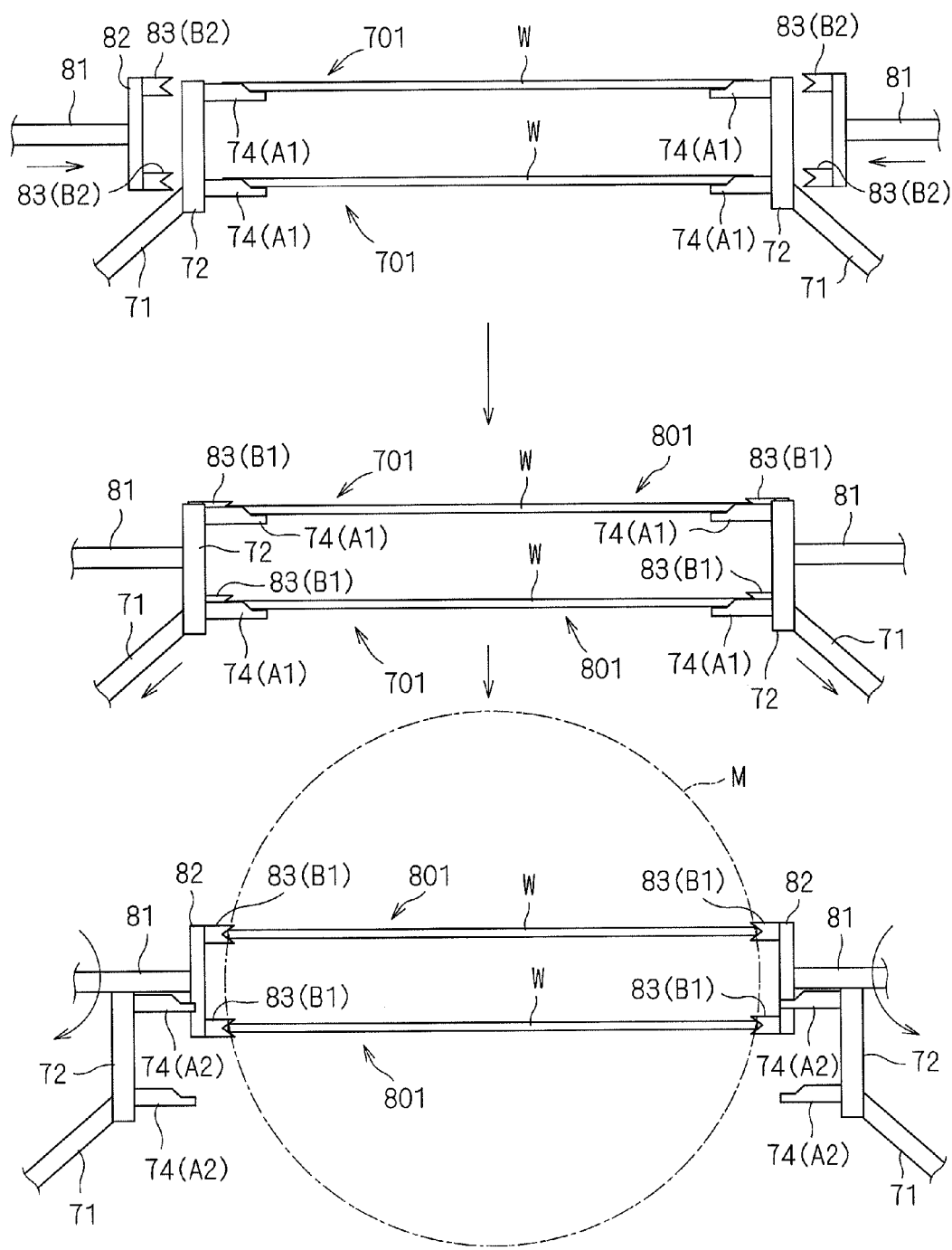
FIG. 11 is a schematic view for explaining the manner of operation of a substrate inverting apparatus.

The manner of operation of the substrate inverting apparatus 100 is explained by reference to FIG. 11 while also adding FIG. 4 to FIG. 10. FIG. 11 is a schematic view for explaining the manner of operation of the substrate inverting apparatus 100. The manner of operation of the substrate inverting apparatus 100 is executed by controlling the respective parts 70, 80, 90 which the substrate inverting apparatus 100 by the control part 60. The substrate inverting apparatus 100 may further include a control part which controls the respective parts 70, 80, 90 mounted on the substrate inverting apparatus 100 in addition to the control part 60 of the substrate processing apparatus 1, and the control part 60 of the substrate processing apparatus 1 may be collectively controlled by the control part 60 of the substrate processing apparatus 1.

Hereinafter, the explanation is made with respect to the operation where the substrate inverting apparatus 100 provided to the invert transfer part 30 inverts the substrate W received from the transfer robot 12 and transfers the substrate W after inverting to the conveyance robot 22. However, the operation where the substrate inverting apparatus 100 inverts the substrate W received from the conveyance robot 22 and the transfer robot 12 is made to receive the substrate W after inverting, and the operation where the substrate inverting apparatus 100 provided to the inverting part 50 inverts the substrate W received from the conveyance robot 22 and the conveyance robot 22 is again made to receive the substrate W after inverting are also equal to the operation explained hereinafter.

In a state where, all support members 74 are arranged at the support position A1 and all clamping members 83 are arranged at the remote position B2, the transfer robot 12 advances two conveyance arms 121a, 121b which respectively support one substrate W into the inside of the casing 301 through the opening 303, and the substrate W supported by the upper-side conveyance arm 121a is supported by the upper-side support portion 701, and the substrate W supported by the lower-side conveyance arm 121b is supported by the lower-side support portion 701. When the substrates W are supported by the respective support portions 701, the transfer robot 12 pulls out the respective conveyance arms 121a, 121b from the inside of the casing 301 through the opening 303. Due to such an operation, two substrates W are transferred to the support mechanism 70 from the transfer robot 12, and two substrates W are brought into a state where two substrates W are supported by two support portions 701 in a state where two substrates W are stacked in a spaced-apart manner in the vertical direction and at a horizontal posture (a state shown in an upper stage of FIG. 11).

When the substrate W is transferred to the substrate inverting apparatus 100, each detection part 90 starts monitoring of the presence or the non-presence of an abnormality. That is, the presence/non-presence detection part 91 starts monitoring of the presence or the non-presence of an abnormality in the object substrate W. Further, the posture abnormality detection part 92 starts monitoring of a posture abnormality of the object substrate W. When the detection part 90 detects the presence or the non-presence of an abnormality or an abnormality in posture, the detection part 90 notifies the occurrence of the abnormality to the control part 60. When the control part 60 receives the notification of the occurrence of the abnormality, the control part 60 executes predetermined error processing (to be more specific, for example, processing notifying the occurrence of the abnormality to an operator while stopping the operation of the apparatus, for example). As described previously, two detection parts 90 are provided to the substrate inverting apparatus 100 and hence, the detection parts 90 can surely detect an abnormality which may occur in the respective substrates W. Accordingly, two substrates W can be safely inverted. Further, when it is confirmed that there is no abnormality in two substrates W (that is, when the presence of the object substrate W is confirmed by the presence/non-presence detection part 91 and it is confirmed by the posture abnormality detection part 92 that the object substrate W is in a horizontal posture) each time the respective operations are performed in the substrate inverting apparatus 100, the processing can be immediately advanced to the next operation and hence, a series of operations relating to the inverting of the substrate W can be performed without a delay whereby a time required for inverting the substrate W can be also shortened.

When all support members 74 are moved to the support position A1 from the standby position A2, subsequently, the cylinders 86 moves the gutter portions 85 to the closed-side end portion position C1 from the open-side end portion position C2. Then, the clamping members 83 are made to approach the substrate W in a state where the clamping members 83 are supported by the cylinders 86 while receiving an elastic biasing force from the elastic members 84 up to a middle stage of such approaching, and the clamping members 83 are moved to the clamping position B1 by receiving the elastic biasing force from the elastic member 84 from the middle stage of the approaching. By arranging the a pair of respective clamping members 83 up to the clamping position B1, the substrate W is brought into a state where both end portions of the substrate W are clamped by the pair of the clamping members 83. That is, the substrate W which is supported by the respective support portions 701 is brought into a state where the substrate W is also clamped by the clamping portions 801 while being supported by the support portions 701 (a state shown in a middle stage in FIG. 11).

When the open-/close detection part 800 detects a closed state, subsequently, all support members 74 are moved synchronously from the support position A1 to the standby position A2 by driving the cylinders 73. Accordingly, the respective support members 74 are brought into a state where the respective support members 74 are arranged outside an inverting region M of the substrate W, and two substrates W are brought into a state where two substrates W are clamped by two clamping portions 801 in a state where two substrates W are stacked in a spaced-apart manner in the vertical direction and in a horizontal posture (a state shown in a lower stage in FIG. 11). However, as described previously, the cylinders 73 move the respective support members 74 to the standby position A2 from the support position A1 by moving the respective support members 74 in the oblique downward direction. Due to such a constitution, the support members 74 are moved in the direction away from both the side surfaces and the lower surface of the substrate W simultaneously. For example, when the support members are moved in the directions away from only the side surfaces of the substrate W, the support members which are brought into a contact with the lower surfaces of the substrate W at the support position A1 are moved while being in contact with the substrate W thus giving rise to a possibility that the lower surface of the substrate W is damaged. On the other hand, when the support members are moved in the direction away from only the lower surface, the support members impinge on the substrate W on a lower side. According to the constitution of this embodiment, such a state does not arise. That is, the support members 74 can be properly moved to the standby position A2 without damaging the substrate W by the support members 74.

When all support members 74 are moved to the standby position A2 from the support position A1, subsequently, the rotary shaft portions 87a, 87b are rotated by 180° about the axis of rotation L by driving the motor 89. As a result, the pair of slide shaft portions 81 is also rotated by 180° about the axis of rotation L, and the supporting columns 82 connected to the respective slide shaft portions 81 are rotated by 180° about a center portion thereof in the extending direction in a vertical plane. Accordingly, the substrate W which is clamped by two respective clamping portions 801 is inverted by 180°. That is, two substrates W are inverted by 180° at a time.

When two substrates W are inverted, subsequently, all support members 74 are moved to the support position A1 from the standby position A2 simultaneously, by driving the cylinders 73. Accordingly, the substrate W after inverting which is clamped by the respective clamping portions 801 is brought into a state where the substrate W is also supported by the support portion 701 while being clamped by the clamping portion 801 (see a middle stage in FIG. 11).

When all support members 74 are moved to the support position A1 from the standby position A2, subsequently, the cylinders 86 move the gutter portions 85 to the open-side end portion position C2 from the closed-side end portion position C1. As a result, the clamping members 83 are moved to the remote position B2 from the clamping position B1. Accordingly, the respective clamping members 83 are brought into a state where the respective clamping members 83 are arranged at positions spaced-apart from the substrate W, and two substrates W are brought into a state where two substrates W are supported by two support portions 701 in a state where two substrates W are vertically stacked in a spaced-apart manner in a horizontal posture (see an upper stage in FIG. 11). In such a state, the conveyance robot 22 makes two conveyance arms 221a, 221b advance into the inside of the casing 301 through the opening 302, and the substrate W supported by the respective support portions 701 is transferred to the respective conveyance arms 221a, 221b and, thereafter, two conveyance arms 221a, 221b which support the substrate W thereon are removed from the casing 301 through the opening 302.

<4. Modification>

In the above-mentioned embodiment, the support mechanism 70 is configured such that the cylinders 73 slidably move the oblique shaft portions 71 which support the support members 74 in the oblique downward direction thus moving the respective support members 74 to the standby position A2 from the support position A1. However, a mode in which the respective support members 74 are moved to the standby position A2 from the support position A1 is not limited to such a mode.

Figure 12:
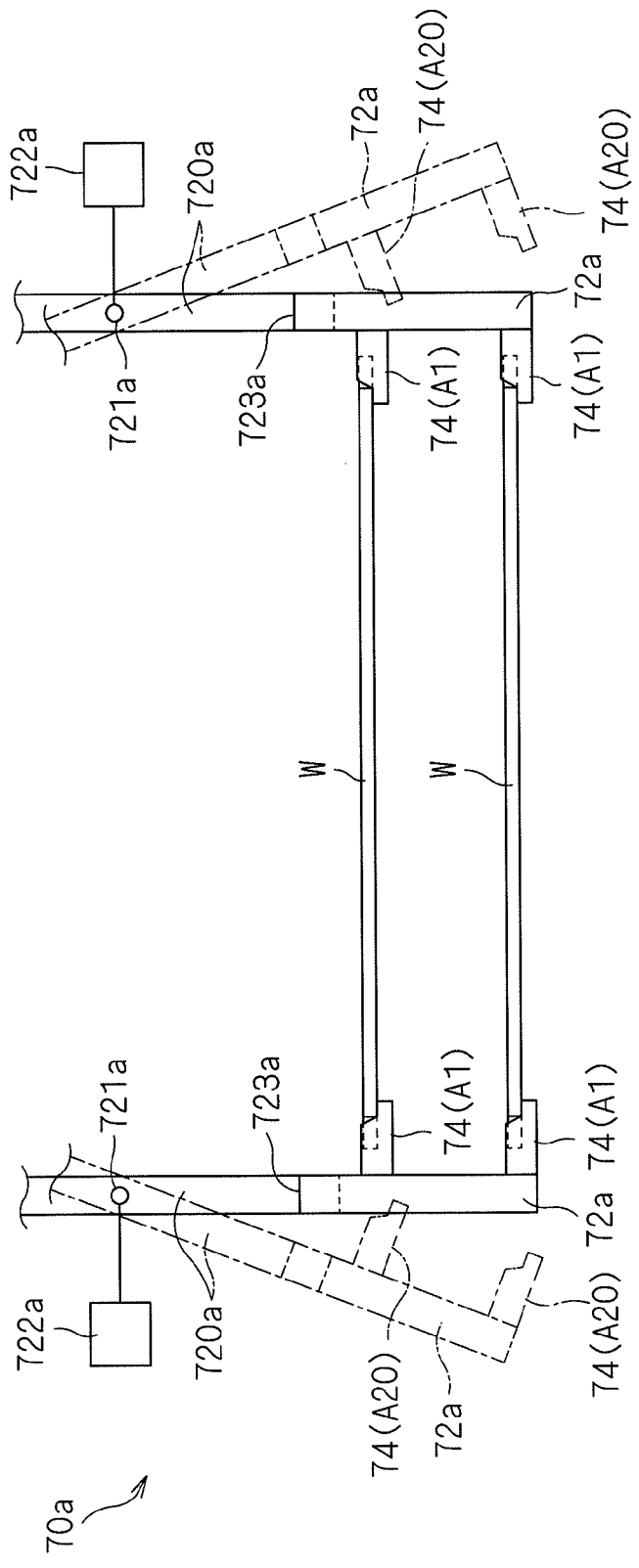
FIG. 12 is a view schematically showing a support mechanism according to a modification.

FIG. 12 exemplifies a support mechanism 70a according to another mode. However, in FIG. 12, the constitution other than portions of the support mechanism 70a and a substrate W supported by the support mechanism 70a are not described in the drawing, and the constitutional elements which do not differ from the constitutional elements explained above are described using the same symbols.

In the same manner as the supporting columns 72 provided to the support mechanism 70 according to the above-mentioned embodiment, on supporting columns 72a provided to the support mechanism 70a according to this modification, support members 74 which extend in the lateral direction in a horizontal plane are also mounted in a cantilever manner. Respective upper end portions of two supporting columns 72a arranged in the fore-and-aft direction are respectively connected to a front-side end portions and back-side end portions of connecting rods 723a extending in the fore-and-aft direction. A support rod 720a which extends in the vertical direction is arranged at a center portion of each connecting rod 723a in the extending direction. An upper end portion of the support rod 720a is connected to a rotary shaft portion 721a extending in the fore-and-aft direction in a horizontal plane, and the rotary shaft portion 721a is made rotatable upon receiving driving of a motor 722a. Accordingly, when the motor 722a rotates the rotary shaft portion 721a, the support rod 720a is tilted about the rotary shaft portion 721a so that two supporting columns 72a which are connected to each other by way of the connecting rod 723a are tilted about the rotary shaft portion 721a synchronously.

In such a constitution, when the motor 722a drives the rotary shaft portion 721a so that the respective supporting columns 72a are tilted in the direction that free ends of the respective supporting columns 72a are moved away from a lateral center line of the substrate W in a state where the support member 74 is at the support position A1 (that is, the position at which the support member 74 is brought into the contact with a lower surface of the substrate W thus supporting the substrate W), the respective support members 74 are moved downward while being moved away from the lateral center line of the substrate W. In this manner, the support member 74a at the support position A1 can be moved to a predetermined standby position A20 where the support member 74a is spaced apart from a lower surface and side surfaces of the substrate W.

In the above-mentioned embodiment, the substrate inverting apparatus 100 is configured to simultaneously invert two substrates W. However, the substrate inverting apparatus 100 may be configured to simultaneously invert three or more substrates W. For example, in the support mechanism 70, four support members 74 may be arranged on the respective supporting columns 72 and, at the same time, in the clamping and inverting mechanism 80, four clamping members 83 may be arranged on the respective supporting columns 82. In this case, four substrates W can be simultaneously inverted.

Further, in the above-mentioned embodiment, the posture abnormality detection part 92 is constituted of two pairs of light emitting parts and the light receiving parts. However, the posture abnormality detection part 92 may be formed of only one pair of the light emitting part and the light receiving part. In this case, it is preferable that light having a large width in cross section be adopted as light emitted from the light emitting part, and the light emitting part be arranged such that the longitudinal direction in the cross section is parallel to a main surface of the substrate W. Also due to such a constitution, by monitoring an amount of light received by the light receiving part, when a posture abnormality of the corresponding substrate W occurs, such a posture abnormality can be immediately detected.

In the above-mentioned embodiment, it is not always necessary to set the number of placement parts PASS provided to the placement unit 40 of the substrate processing apparatus 1 to six. The layouts of the front surface cleaning processing part SS and the back surface cleaning processing part SSR in the respective cleaning processing units 21a, 21b of the substrate processing apparatus 1 and the mounting number of the respective processing parts are not limited to the above-mentioned layout and numbers. The inverting part 50 is not always necessary to be arranged on the placement unit 40 in a stacked manner. For example, the inverting part 50 may be arranged in the cleaning processing cell 20.

Further, in the above-mentioned embodiment, the substrate inverting apparatus 100 which is configured such that scrub cleaning processing is applied to the substrate W mounted on the substrate processing apparatus 1 has been exemplified. However, the substrate inverting apparatus 100 may be mounted on various substrate processing apparatuses which apply various processing to the substrate W. For example, the substrate inverting apparatus 100 may be configured such that a cell which performs resist coating processing and a cell which performs developing processing are mounted on a coater and a developer which are arranged parallel to each other with a substrate transfer part sandwiched therebetween.

Although the present invention has been explained in detail heretofore, the above-mentioned explanation is provided only as examples in all phases, and the present invention is not limited by the examples. It should be construed that innumerous non-exemplified modifications are conceivable without departing from the scope of the present invention.

REFERENCE SIGNS LIST 1 substrate processing apparatus
10 indexer cell
12 transfer robot
20 cleaning processing cell
22 conveyance robot
30 inverting and transferring part
50 inverting part
40 placement unit
60 control part
100 substrate inverting apparatus
70, 70a support mechanism
80 clamping and inverting mechanism
90 detection part
91 presence/non-presence detection part
W substrate

The invention claimed is:

1. A substrate inverting apparatus for inverting a substrate, the substrate inverting apparatus comprising:
a support mechanism which supports a plurality of substrates in a state where the substrates are stacked vertically in a spaced-apart manner in a horizontal posture; and a clamping and inverting mechanism which clamps said plurality of substrates supported by said support mechanism respectively and inverts said plurality of substrates at a time, wherein
said clamping and inverting mechanism comprises:
a pair of clamping members which clamps each one of said plurality of substrates from both edge portions;
a clamping member drive part which moves said pair of respective clamping members between a near position where a part of the clamping members is arranged close to or is brought into contact with a side surface of the substrate, and a remote position where said clamping members are away from said side surface; and an elastic member which elastically biases said clamping members arranged at said near position toward the side surface of said substrate,
said support mechanism comprises:
a plurality of support members which support said plurality of respective substrates from a lower surface side thereof; and a support member drive part which moves said plurality of respective support members between a support position where a part of the support member is brought into contact with a lower surface of the substrate, and a standby position where said support member is away from said lower surface, and
said support member drive part moves the support member to said standby position from said support position by moving said plurality of respective support members downward while moving said support members away from the center of said substrate as viewed in the vertical direction.

2. The substrate inverting apparatus according to claim 1, further comprising a detection part which is provided corresponding to each one of said plurality of respective substrates supported by said support mechanism and detects an abnormality of the corresponding substrate.

3. The substrate inverting apparatus according to claim 2, wherein said detection part includes a first light emitting part and a first light receiving part, and said first light emitting part and said first light receiving part are arranged to face each other in an opposed manner with the substrate being made to correspond to the detection part sandwiched therebetween as viewed in the vertical direction, and said first light emitting part and said first light receiving part are arranged above and below said substrate separately.

4. The substrate inverting apparatus according to claim 2, wherein said detection part includes a second light emitting part and a second light receiving part, and said second light emitting part and said second light receiving part are arranged to face each other in an opposed manner with the substrate being made to correspond to the detection part sandwiched therebetween as viewed in the vertical direction, and said second light emitting part and said second light receiving part are arranged in the same horizontal plane disposed adjacent to a main surface of said substrate.

5. The substrate inverting apparatus according to claim 4, wherein said detection part includes a third light emitting part and a third light receiving part, and said third light emitting part and said third light receiving part are arranged to face each other in an opposed manner with the substrate being made to correspond to the detection part sandwiched therebetween as viewed in the vertical direction, and said third light emitting part and said third light receiving part are arranged in the same horizontal plane disposed adjacent to the main surface of said substrate, and
a straight line which connects said second light emitting part and said second light receiving part, and a straight line which connects said third light emitting part and said third light receiving part are arranged non-parallel to each other.

6. The substrate inverting apparatus according to claim 1, wherein said clamping and inverting mechanism comprises an opening and closing detection part which detects whether said pair of respective clamping members is at said remote position or at said near position.

7. A substrate processing apparatus comprising:
a substrate inverting apparatus which inverts a substrate;
a front surface cleaning part which cleans a front surface of the substrate;
a back surface cleaning part which cleans a back surface of the substrate; and
a first conveyance robot which conveys the substrate between said front surface cleaning part, said back surface cleaning part and said substrate inverting apparatus, wherein
said substrate inverting apparatus comprises:
a support mechanism which supports a plurality of substrates in a state where the substrates are stacked vertically in a spaced-apart manner in a horizontal posture; and a clamping and inverting mechanism which clamps said plurality of substrates supported by said support mechanism respectively and inverts said plurality of substrates at a time, wherein said clamping and inverting mechanism comprises:
a pair of clamping members which clamps each one of said plurality of substrates from both edge portions;
a clamping member drive part which moves said pair of respective clamping members between a near position where a part of the clamping members is arranged close to or is brought into contact with a side surface of the substrate, and a remote position where said clamping members are away from said side surface; and an elastic member which elastically biases said clamping members arranged at said near position toward the side surface of said substrate,
said support mechanism comprises:
a plurality of support members which support said plurality of respective substrates from a lower surface side thereof; and a support member drive part which moves said plurality of respective support members between a support position where a part of the support member is brought into contact with a lower surface of the substrate, and a standby position where said support member is away from said lower surface, and
said support member drive part moves the support member to said standby position from said support position by moving said plurality of respective support members downward while moving said support members away from the center of said substrate as viewed in the vertical direction.

8. The substrate processing apparatus according to claim 7, further comprising:
a processing block where said front surface cleaning part, said back surface cleaning part and said first conveyance robot are arranged; and an indexer block where a second conveyance robot is arranged, and the second conveyance robot transfers a non-processed substrate to said processing block and receives a processed substrate from said processing block,
said substrate inverting apparatus is provided at a connecting portion between said indexer block and said processing block, wherein
when either one of said first conveyance robot and said second conveyance robot conveys the substrate into said substrate inverting apparatus, the substrate inverted by said substrate inverting apparatus is delivered by the other conveyance robot.

* * * * *